(12) United States Patent
Tan et al.

(10) Patent No.: US 9,675,498 B2
(45) Date of Patent: Jun. 13, 2017

(54) ABSORBENT ARTICLE WITH NON-UNIFORM DIMENSIONED SIDE BARRIERS

(71) Applicant: Kimberly-Clark Worldwide, Inc., Neenah, WI (US)

(72) Inventors: Cai Shan Tan, Seongnam-si (KR); Franz Aschenbrenner, Kastl (DE); Jina Gwag, Gyeonggi-do (KR); DooHong Kim, Yongin-si (KR); SangWook Lee, Antioquia (CO); Meijia Ng, Singapore (SG); SoHyun S. Park, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/279,034

(22) Filed: May 15, 2014

(65) Prior Publication Data
US 2014/0358106 A1    Dec. 4, 2014

Related U.S. Application Data

(60) Provisional application No. 61/829,620, filed on May 31, 2013.

(51) Int. Cl.
*A61F 13/15* (2006.01)
*A61F 13/20* (2006.01)
*A61F 13/475* (2006.01)

(52) U.S. Cl.
CPC ...... *A61F 13/4752* (2013.01); *A61F 13/4756* (2013.01)

(58) Field of Classification Search
CPC .................... A61F 13/4752; A61F 13/4756
See application file for complete search history.

(56) References Cited

U.S. PATENT DOCUMENTS

| | | | |
|---|---|---|---|
| 4,505,705 A | 3/1985 | Matthews et al. |
| 4,623,340 A | 11/1986 | Luceri |
| 5,324,278 A | 6/1994 | Visscher et al. |
| 5,447,507 A | 9/1995 | Yamamoto |
| 5,542,941 A | 8/1996 | Morita |
| 5,575,785 A | 11/1996 | Gryskiewicz et al. |
| 5,599,337 A | 2/1997 | McCoy |
| 5,624,423 A | 4/1997 | Anjur et al. |

(Continued)

FOREIGN PATENT DOCUMENTS

| | | |
|---|---|---|
| CN | 2334381 Y | 8/1999 |
| CN | 2436133 Y | 6/2001 |

(Continued)

*Primary Examiner* — Michele M Kidwell
(74) *Attorney, Agent, or Firm* — Kimberly-Clark Worldwide, Inc.

(57) ABSTRACT

An absorbent article has non-uniform dimensioned side barrier features and includes a lower structure. The article also includes an upper structure in fluid communication with the lower structure. The upper structure is adjacent and bonded to the lower structure. Embossment channels or embossment features and said side barrier feature lateral-most edges define side barrier features having either non-uniform lateral width dimensions or a combination of non-uniform lateral width and non-uniform height dimensions along the longitudinal direction of said article.

23 Claims, 12 Drawing Sheets

(56) References Cited

U.S. PATENT DOCUMENTS

| | | | |
|---|---|---|---|
| 5,713,885 A | 2/1998 | Jorgenson et al. | |
| 5,746,732 A | 5/1998 | Olsson et al. | |
| 5,795,344 A | 8/1998 | Chappell | |
| 5,807,367 A | 9/1998 | Dilnik et al. | |
| 5,843,067 A | 12/1998 | Trombetta et al. | |
| 5,921,975 A | 7/1999 | Suzuki et al. | |
| 6,159,190 A | 12/2000 | Tanaka et al. | |
| 6,175,056 B1 | 1/2001 | Carlucci et al. | |
| 6,410,822 B1 | 6/2002 | Mizutani | |
| 6,616,644 B1 | 9/2003 | Mizutani | |
| 6,902,552 B2 | 6/2005 | VanGompel et al. | |
| 7,078,583 B2 * | 7/2006 | Kudo | A61F 13/47218 604/378 |
| 7,976,525 B2 | 7/2011 | McDaniel | |
| 2001/0020157 A1 | 9/2001 | Mizutani et al. | |
| 2002/0120247 A1 | 8/2002 | Mizutani et al. | |
| 2002/0157771 A1 | 10/2002 | Kusagawa et al. | |
| 2004/0249355 A1 | 12/2004 | Tanio et al. | |
| 2005/0085783 A1 * | 4/2005 | Komatsu | A61F 13/4704 604/385.04 |
| 2005/0124951 A1 | 6/2005 | Kudo et al. | |
| 2005/0148972 A1 | 7/2005 | Miyama et al. | |
| 2005/0256472 A1 | 11/2005 | Tsutsui | |
| 2006/0271008 A1 * | 11/2006 | Tanio | A61F 13/47263 604/385.31 |
| 2007/0055212 A1 | 3/2007 | Kameo et al. | |
| 2007/0087169 A1 * | 4/2007 | McFall | A61F 13/511 428/172 |
| 2011/0046596 A1 | 2/2011 | Kudo et al. | |
| 2012/0296303 A1 | 11/2012 | Ng et al. | |

FOREIGN PATENT DOCUMENTS

| | | |
|---|---|---|
| EP | 0 606 082 A1 | 7/1994 |
| EP | 0 726 751 B1 | 3/2000 |
| GB | 2 319 730 A | 6/1998 |
| JP | 2007-089906 A | 4/2007 |
| KR | 10-2009-0054960 A | 6/2009 |
| WO | WO 92/07535 A1 | 5/1992 |
| WO | WO 94/16658 A1 | 8/1994 |
| WO | WO 95/15139 A1 | 6/1995 |
| WO | WO 98/43585 A1 | 10/1998 |
| WO | WO 01/24750 A1 | 4/2001 |
| WO | WO 2012/119353 A1 | 9/2012 |

* cited by examiner

ABSORBENT ARTICLE WITH NON-UNIFORM DIMENSIONED SIDE BARRIERS

This non-provisional application claims the benefit of priority from U.S. Provisional Application No. 61/829,620 filed on May 31, 2013. The entirety of Application No. 61/829,620 is incorporated herein by reference.

FIELD OF THE INVENTION

The present invention relates to absorbent personal care articles with side barrier and pillowy features, to control leakage of fluid off of an article's side edges and also to provide comfort next to the skin of a consumer. More particularly, it relates to absorbent side barrier features for feminine hygiene and adult care absorbent personal care articles.

BACKGROUND

Absorbent personal care articles such as feminine hygiene products, adult care incontinence products and baby and child care diaper products are often placed in a user's undergarments, or between a user's body and outergarments to capture body fluids. Absorbent personal care articles traditionally include on their chassis at least a user-facing, topsheet or cover layer, that contacts the skin of a consumer during use, a garment-facing, backsheet layer that prevents leakage of body fluid through the backside surface of the article, and an absorbent core layer sandwiched between the topsheet layer and the backsheet layer, that absorbs and retains body fluid which is received through the topsheet layer. In feminine hygiene articles such as napkins, pads, and liners, adult care incontinence articles such as pads, inserts, briefs and diapers, and baby diapers, body fluids may have a tendency to flow off the article lateral side edges toward the user's legs in the crotch region. For feminine care pads, napkins, and liners, this directional movement is often near the article "wings," "flaps," or "tabs" (if present), the "wings," "flaps," or "tabs" being layer extensions that are used to hold the article to the user's undergarments.

To address such leakage, manufacturers of absorbent articles often incorporate additional side barrier features to provide fluid leakage protection. Such leakage protection is designed to prevent body fluids, such as urine, feces, or menses from running over or through the lateral side edges of the article, and subsequently staining a user's undergarments, outergarments or bedding. A traditional side barrier feature may incorporate an additional layer or structure (which provides elevation above the plane of the absorbent core layer within the article) for physically blocking the flow of fluid past the lateral side edges of the article. Examples of such additional structures include strips of absorbent or non-absorbent material, such as those described in U.S. Pat. No. 5,599,337 to Mccoy, U.S. Pat. No. 5,624,423 to Anjur et al., U.S. Pat. No. 5,713,885 to Jorgenson et al., and U.S. Pat. No. 5,807,367 to Dilnik et al., as well as those illustrated in CN 2436133Y. Such wall-like structures may be effective in reducing or eliminating side leakage, but require additional layer costs, and complicated manufacturing methods for cutting and/or placement of the structures on the article chassis. Further, such wall-like structures have parallel side edges which interfere with user comfort, being non-conforming to a user's inner thigh regions (crotch area) when in use.

Alternatively, such side barrier features may be formed from loops or folds in the topsheet layer or other additional layers on absorbent articles, as can be seen for example, in United States Publication 2001/020157 to Mizutani et al. As noted with the separate elevated structures previously described, such loops or folds may present complex manufacturing challenges and at additional costs. While targeted placement of walls only along certain regions of a lateral side edge is known, such as the discrete wall sections adjacent an article wing seen in U.S. Pat. No. 5,447,507 to Yamamoto, such additional structure requires relatively complex manufacturing steps and do not, in-and-of themselves, provide additional absorbency.

Other side barrier structures have employed elastic strands or elasticized portions along the side edges of an article, or alternatively, shrinkable strand material, to elevate portions of a topsheet layer of an article substantially above the plane of the absorbent layer, which provides for a close-to-body fit of the side barrier feature. Such elastic feature may be present in the article as it is initially obtained by the consumer. Alternatively, a shrinkable feature may be activated in an article only upon the occurrence of an event, such as later contact with body fluid or heat from a consumer during use. Such elastic or shrinkable side barrier features are frequently employed in both baby and child care absorbent articles, such as in diapers, as well as in feminine hygiene and adult care incontinence absorbent articles, such as in sanitary and adult care pad inserts. Elastic or shrinkable side barrier features are described for example, in U.S. Pat. No. 6,902,552 to VanGompel et al., in United States Publications 2012/296303 to Ng et al. and Mizutani noted above, as well as in European Publication EP0606082 to McDaniel. While these elastic or shrinkable features may be effective in blocking the flow of body fluids off of the article and/or containing the fluid in a cup-like configuration, such elastic or shrinkable materials are often constructed from expensive polymeric materials, which add significantly to the overall cost of the absorbent article, as well as to the complexity of the article manufacturing process. Even with the variety of side barrier features described above, there is still a need for effective side barrier features that are formed with absorbent structures, and that provide targeted barrier dimensions along specific portions of the lateral side edges of absorbent articles. There is a further need for barrier structures which do not incur expensive material costs or require complex manufacturing steps for their implementation. For example, there is a need for such barrier features which may be formed from previously existing non-barrier layers of an article.

Embossing channels or grooves have also been used to create wall-like, topographical features, in order to slow the movement of fluid to, or past the lateral side edges of an article. An example of such embossing channels may be found in U.S. Pat. No. 5,795,344 to Chappell. Such embossing channels or grooves may be of any number of shapes and/or patterns, may be located in a number of positions on the article, such as the rectangular, peripherally-placed channel in Chappell, or alternatively arcs, such as those illustrated in U.S. Pat. No. 6,410,822 to Mizutani. Still further known embossment channel shapes may include racetrack or dogbone designs, or discrete patterns. However, even with such variety of embossed channel shapes and embossment positions, there is a need for enhanced barrier structures which offer both non-uniform dimensioned absorbent functionality, above the plane of the main absorbent layer of an article. Such non-uniform dimensioned absorbent functionality could provide for targeted barrier protection in certain areas/regions along an article side edge, without wasting article construction materials and without adding additional material costs to an absorbent article.

Finally, "compound" absorbent pads are also known in the feminine hygiene area. Such are exemplified by international publication WO1998/43585 to Chatterjee. However, even with such compound pads, there is still a need for pads with absorbent barriers that are targeted to provide enhanced protection along high-leakage areas of such pads, and which are cost effective (not requiring extra materials or complex construction steps).

SUMMARY OF THE INVENTION

In one embodiment of the invention, an absorbent article having non-uniform dimensioned side barrier features has a longitudinal direction, a transverse direction and a depth direction, longitudinally directed side edges and longitudinal ends. The absorbent article includes a lower structure having longitudinally directed side edges, the lower structure including a backsheet layer, a first fluid permeable topsheet layer bonded to the backsheet layer, and a first absorbent core layer sandwiched between the first fluid permeable topsheet layer and the backsheet layer. The first absorbent core layer has lateral-most side edges. The absorbent article also includes an upper structure in fluid communication with the lower structure, with the upper structure being adjacent and bonded to the lower structure on the first fluid permeable topsheet layer, and including a second fluid permeable topsheet layer and at least one absorbent additional layer selected from at least one of the group consisting of a transfer layer, a second absorbent core layer, and a lofty layer. The second topsheet layer is folded about the at least one absorbent additional layer to create substantially straight side barrier feature lateral-most edges. The side barrier feature lateral-most edges are either inboard of the lateral-most side edges of the first absorbent core layer or generally aligned along the depth direction with the lateral-most side edges of the first absorbent core layer. The upper structure is bonded to the lower structure at or immediately adjacent the side barrier feature lateral-most edges, at least at one of the article longitudinal ends. The upper structure includes embossment channels or embossment features, concave or indented with respect to the side barrier feature lateral-most edges, and the embossment channels or embossment features are within at least two layers of the article. The embossment channels or embossment features and the side barrier feature lateral-most edges define side barrier features having either non-uniform lateral width dimensions, non-uniform height dimensions or a combination of non-uniform lateral width and non-uniform height dimensions along the longitudinal direction of the article.

In an alternative embodiment of the invention, the absorbent article has an upper structure which includes a second fluid permeable topsheet layer, and a transfer layer subjacent the second fluid permeable topsheet layer. In yet another alternative embodiment of the invention, the absorbent article includes an upper structure having a second fluid permeable topsheet layer and a second absorbent core layer subjacent the second fluid permeable topsheet layer. In still another alternative embodiment of the invention, the absorbent article includes an upper structure having a second absorbent core layer subjacent a transfer layer.

In yet another alternative embodiment of the invention, the embossment channels comprise continuous concave channels separated by a minimum distance of between about 20 and 40 mm. In another alternative embodiment of the invention, the absorbent article further includes wings extending laterally along the article longitudinally directed side edges. In another alternative embodiment of the invention, the absorbent article side barrier features have a lateral width range of between an amount greater than 0, to about 12 mm, and where the widest lateral width is positioned adjacent to said wings. In another alternative embodiment of the invention, the absorbent article the lateral width is non-uniform along the article longitudinal direction. In another alternative embodiment of the invention, the absorbent article side barrier features have a lateral width of between about 6 and 10 mm in at least one location along the article longitudinal direction. In another alternative embodiment of the invention, the absorbent article side barrier features have a height range of between about 1 and 12 mm along the article longitudinal direction, and the largest side barrier height is positioned adjacent to article wings. In another alternative embodiment of the invention, the absorbent article side barrier features are positioned closer to one longitudinal end than the other longitudinal end. In still another alternative embodiment of the invention, the absorbent article includes embossment channels or embossment features that extend downwardly through at least three layers within the article. In another alternative embodiment of the invention, the absorbent article includes embossment channels or embossment features that extend downwardly through at least four layers within the article. In yet another alternative embodiment of the invention, the absorbent article includes a first fluid permeable topsheet layer that is noncontinuous along the transverse direction.

In another alternative embodiment of the invention, the absorbent article upper structure has a basis weight of all layers excluding the second fluid permeable topsheet layer of between about 18 and 350 gsm. In yet another alternative embodiment of the invention, the absorbent article second fluid permeable topsheet layer does not completely envelop the absorbent additional layer or layers. In another alternative embodiment of the invention, the absorbent article upper structure includes a second absorbent core layer, and the second absorbent core layer has a second absorbent core layer transverse direction width. In such an embodiment, the first absorbent core layer has a first absorbent core layer transverse width, and the ratio of the second absorbent core layer transverse width to the first absorbent core layer transverse width is between about 0.7 to about 0.9. In another alternative embodiment of the invention, the absorbent article side barrier features are not affixed to the lower structure along their lateral-most edges, for a length of between about 70 and 200 mm of the side barrier features. In another alternative embodiment of the invention, the absorbent article side barrier features are not affixed to the lower structure along their lateral-most edges, for a length of between about 110 and 130 mm of the side barrier features. In still another alternative embodiment of the invention, the absorbent article side barrier features demonstrate a non-uniform lateral width dimension along the article longitudinal direction. In another alternative embodiment of the invention, the absorbent article side barrier features demonstrate a non-uniform height dimension along the article longitudinal direction. In another alternative embodiment of the invention, the absorbent article side barrier features demonstrate a non-uniform lateral width and non-uniform height dimension along the article longitudinal direction. In another alternative embodiment of the invention, the absorbent article includes a central longitudinal direction and the side barrier features are symmetrically positioned about the article central longitudinal direction. In another alternative embodiment of the invention, the absorbent article includes side barrier features closer to one article longitudinal end than the other article longitudinal end. In yet another alternative embodiment of the invention, the absorbent article includes side barrier features that are visually highlighted. In yet another alternative embodiment of the invention, the absorbent article upper structure is bonded to the lower structure at the side barrier feature lateral-most edges, at both of the article longitudinal ends. In another alternative embodiment of the invention, the absorbent article upper structure is bonded to the lower structure at the side barrier feature lateral-most edges, at one of the article longitudinal ends and also at a position substantially inboard of the other article longitudinal end, at a position towards the center of the pad.

BRIEF DESCRIPTION OF THE DRAWINGS

A full and enabling disclosure of the present invention is set forth more particularly in the remainder of the specification, including reference to the accompanying figures, in which.

DESCRIPTION OF THE INVENTION

Figure 1:
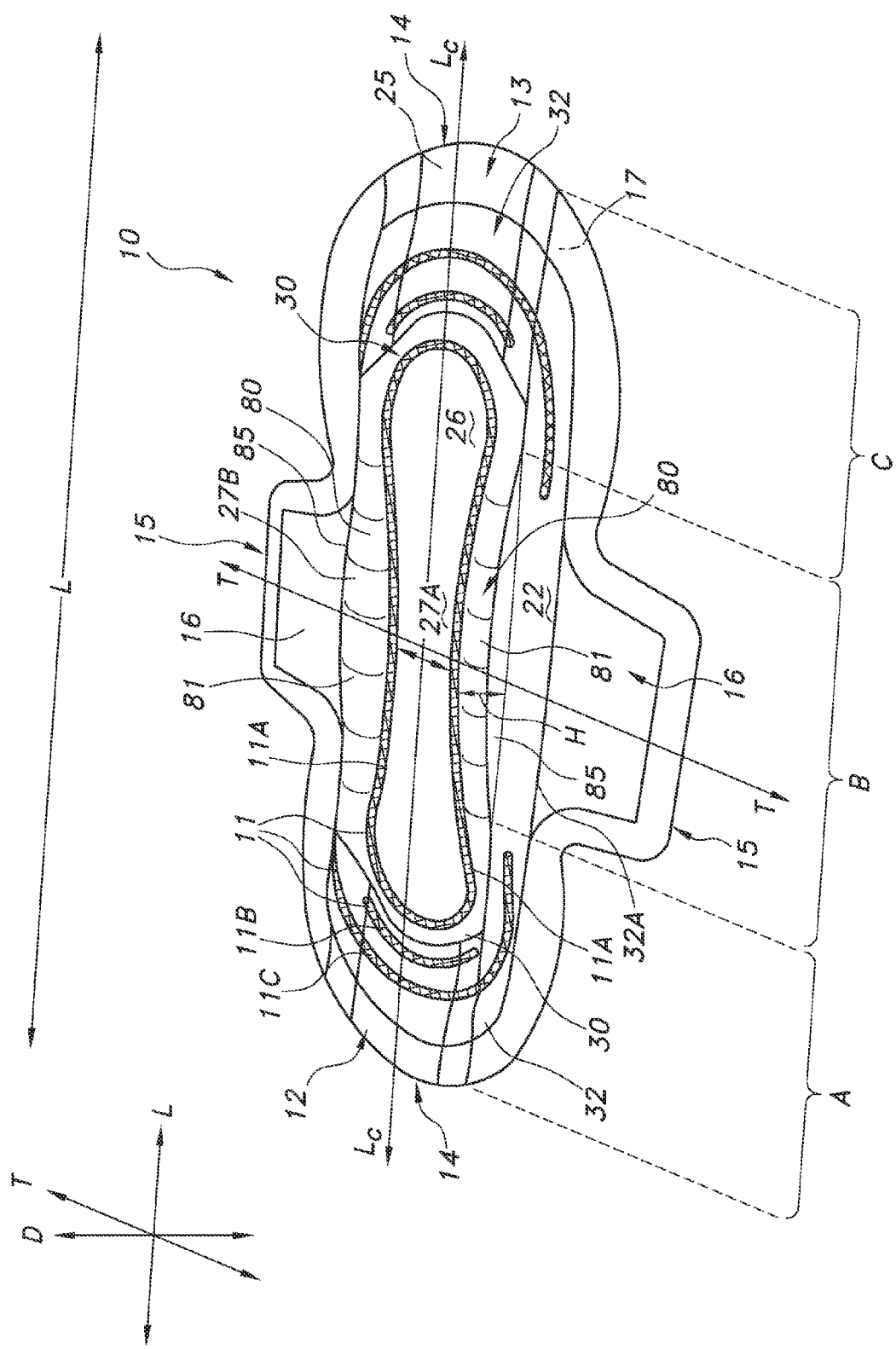
FIG. 1 is a perspective view of one embodiment of an absorbent article of the invention, in the form of a feminine hygiene pad.

Reference now will be made in detail to various embodiments of the invention, one or more examples of which are set forth below. Each example is provided by way of explanation of the invention, not a limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not being expressly illustrated in every view or location, it should be understood that traditional absorbent article construction adhesive may be used between each of the various article layers, for securement of the layers within the article. Certain highlighted areas of either desired adhesive attachment, or adhesive absence, will also be presented throughout the text.

The articles of the present invention include an upper layered structure and a lower layered structure. Each of the upper layered and lower layered structures include a topsheet (which may be the same for both layers, or different from one another). It has been found, that by incorporating a topsheet layer that at least partially envelops an absorbent layer, fluid transfer layer, alternative lofty layer or combination thereof, along an absorbent article depth direction, to form the folded, multi-layered upper structure, in conjunction with a concave or otherwise indented embossment feature adjacent the lateral side edges of the article folded upper structure, an elevated and outwardly inclined side barrier feature can be created that provides for targeted barrier protection in areas of high leakage potential on an absorbent article (such as the adjacent wing areas on a feminine care pad), or the longitudinal ends, or both. Such elevated barrier features can be created without the use of additional costly strip materials or layers, and by lower complexity, lower cost manufacturing processes. The produced side barrier feature may be a discrete structure situated on the user-facing surface of the article in only a targeted location near high potential leak areas, or alternatively part of a larger structure which is also situated on the user facing surface of an article, and which includes side barrier features also strategically placed along the larger structure's length adjacent high potential leak areas. If the larger upper layered structure extends from one longitudinal end of the article to the other, such raised side barrier features are desirably placed adjacent the wing areas of an article. In such side barrier features, the inward edge of the barrier, that is, the edge of the barrier that is closest to the central longitudinal direction (axis) of the article, is formed from the concave or indented portion of an embossment channel or feature. The inward edge of the barrier is held to the article by the embossment channel bonding. The outward edge that also defines the side barrier feature and is closest to the side edge of the article, is detached from the article along the lateral-most side barrier edge. The outward edge (lateral-most edge of the side barrier) is in one embodiment, inboard of both the article lateral side edges and the first absorbent core layer lateral-most edge in the article lower layered structure. Alternatively, the outward edge is approximately aligned or coextensive with the lateral-most edge of the first absorbent core layer of the article lower layered structure. The produced barrier features desirably demonstrate both loft and absorbency, being distinct and detached at select portions along their length at their lateral-most edge, from subjacent article layers. The side barrier features, which demonstrate a non-uniform lateral width dimension, and also desirably, a non-uniform height dimension along select portions of the barrier length (created in part by the concave or indented embossed channel position and securement of the side barrier ends to the article longitudinal ends), results in at least a relatively wide, uninterrupted absorbent barrier portion where it is needed most, along the lateral side areas that are to be placed adjacent a user's legs (the crotch region) and near an article wings, if such are present. Such side barrier features may also be of a higher elevation in the high leakage areas. By placement of various elongated embossed concave channels adjacent the longitudinal sides of the absorbent layers, the heights and widths of the barrier features can be controlled.

For the purposes of this application, the term "non-uniform" dimensioned shall refer at least to the lateral width dimension of the side barrier feature between the embossed channel or embossed feature defining one side barrier feature side/edge (also referred to as the inward attached edge), and the side barrier, lateral-most free edge directly across from the embossed channel or embossed feature (which free edge defines a second barrier side, and is also referred to as an outward detached edge). The term "non-uniform" dimensioned shall also, in some embodiments, refer to the height dimension of the side barrier feature in the depth direction, when measured along the side barrier feature length from one end of the article to the other. Such height measurement shall be taken from the highest point of the side barrier feature to the base of the side barrier (above the side barrier feature supporting layer/or lower pad structure). In other words, the lateral width dimension is the dimension of the side barrier feature that is approximately normal to the side barrier lateral-most free edge, as illustrated in the figures. The described non-uniformity, references the varying width, and in some instances, the varying height dimensions when measured along the barrier length. It is desirable that the described free edge (as will be described as lateral-most edge) be a substantially straight edge for ease of manufacture.

While a feminine hygiene pad 10 is illustrated in FIGS. 1-13 as a desirable embodiment of the invention, it should be recognized that any number of absorbent article product categories are contemplated to be within the scope of the invention, such as for example, adult incontinence briefs and pads, as well as baby and child care diapers and training pants. As seen in FIG. 1 which illustrates a top perspective view of such an absorbent article, a feminine hygiene pad 10 includes a longitudinal direction L (or axis), a transverse direction T (or axis), and a depth direction D (or axis) normal to the longitudinal and transverse directions. A central longitudinal direction (or axis) Lc, is also present, as is a central transverse direction Tc, which respectively separate the pad into two symmetrical halves along the longitudinal direction, and in some instances depending on article type, two symmetrical halves along the transverse direction. The feminine hygiene pad 10 includes two longitudinal ends, those being a first longitudinal end 12, and a second longitudinal end 13, each end having a longitudinal end edge 14. The pad (article) 10 also includes lateral side edges 15. The pad desirably includes wings or flaps 16, for securement of the pad to the underside surface of undergarments (not shown), when in use. The wings or flaps fold under the crotch portion of an undergarment and secure the pad wings either to themselves, or directly to the underside surface of the undergarment.

Figure 1A:
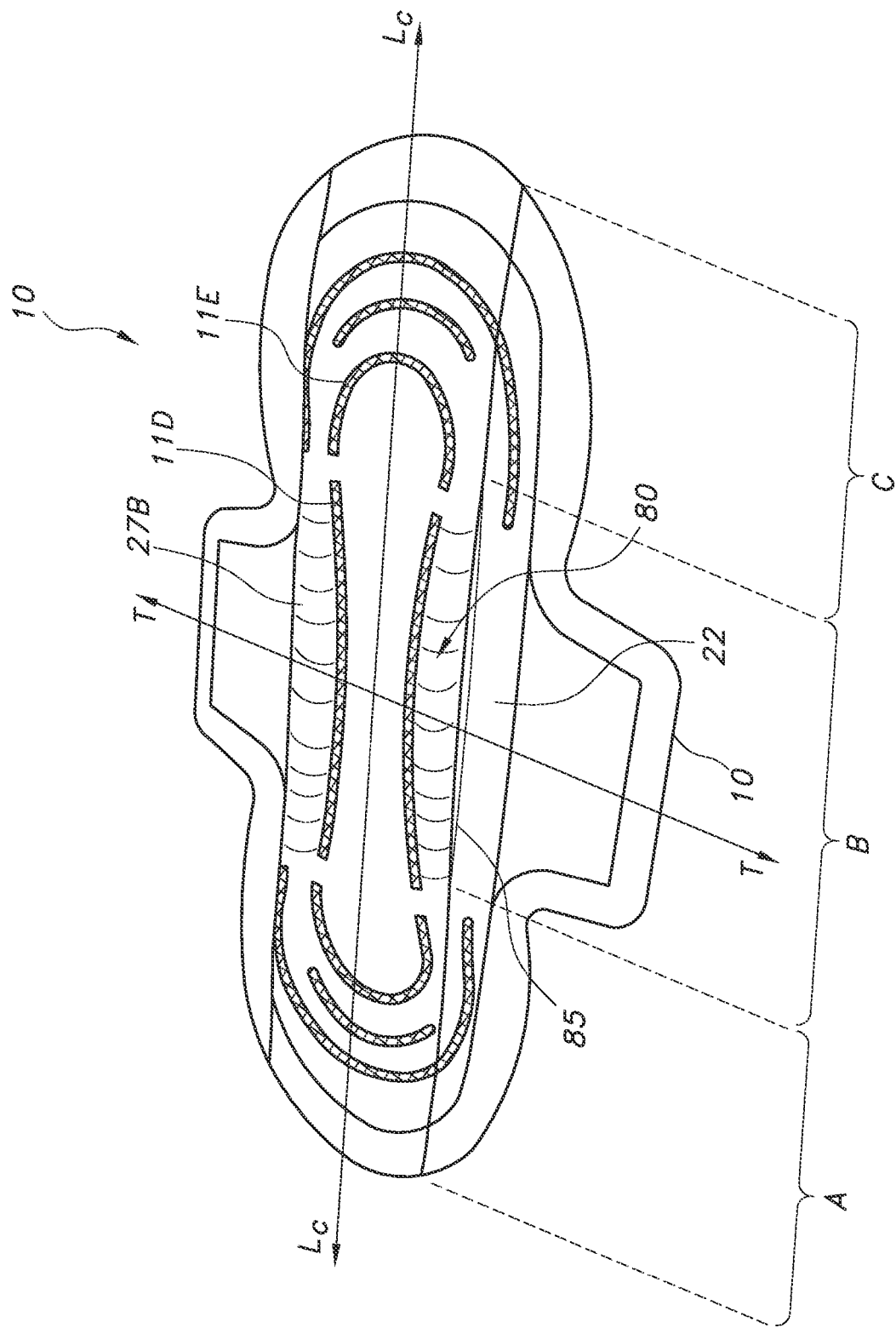
FIG. 1A is a perspective view of an alternative embodiment of an absorbent article of the invention, in the form of a feminine hygiene pad.

The feminine hygiene pad 10 includes a least one, and desirably a series of embossed channels 11 (or other embossed features) that are visible when viewing the article from the second topsheet layer 26, user-facing surface 27 (the second topsheet layer 26 being a user-facing topsheet layer and including folds). In the case of the illustrated pad 10, the embossed channels include a curved and elongated, racetrack-shaped continuous channel, having two concave stretches along the longitudinal direction 11A, a first outer, arc-shaped embossed channel 11B, and a second outer arc-shaped embossed channel 11C. The racetrack-shaped, embossed continuous channel 11A includes two concave portions which are concave with respect to each lateral side edge 15 of the pad (as well as to the lateral-most side edge 85 of the side barrier features 80 to be described). While such concave channels 11A are shown as part of a completely continuous embossment, such concave channels may also be discrete concave arcs 11D as seen in FIG. 1A. Still alternatively, such channels may be partially concave, such as in alternating (not shown), or stepped, wave-like shapes along the longitudinal direction, having desirably at least one prominently deeper concavity (as seen in FIG. 1C).

Figure 1B:
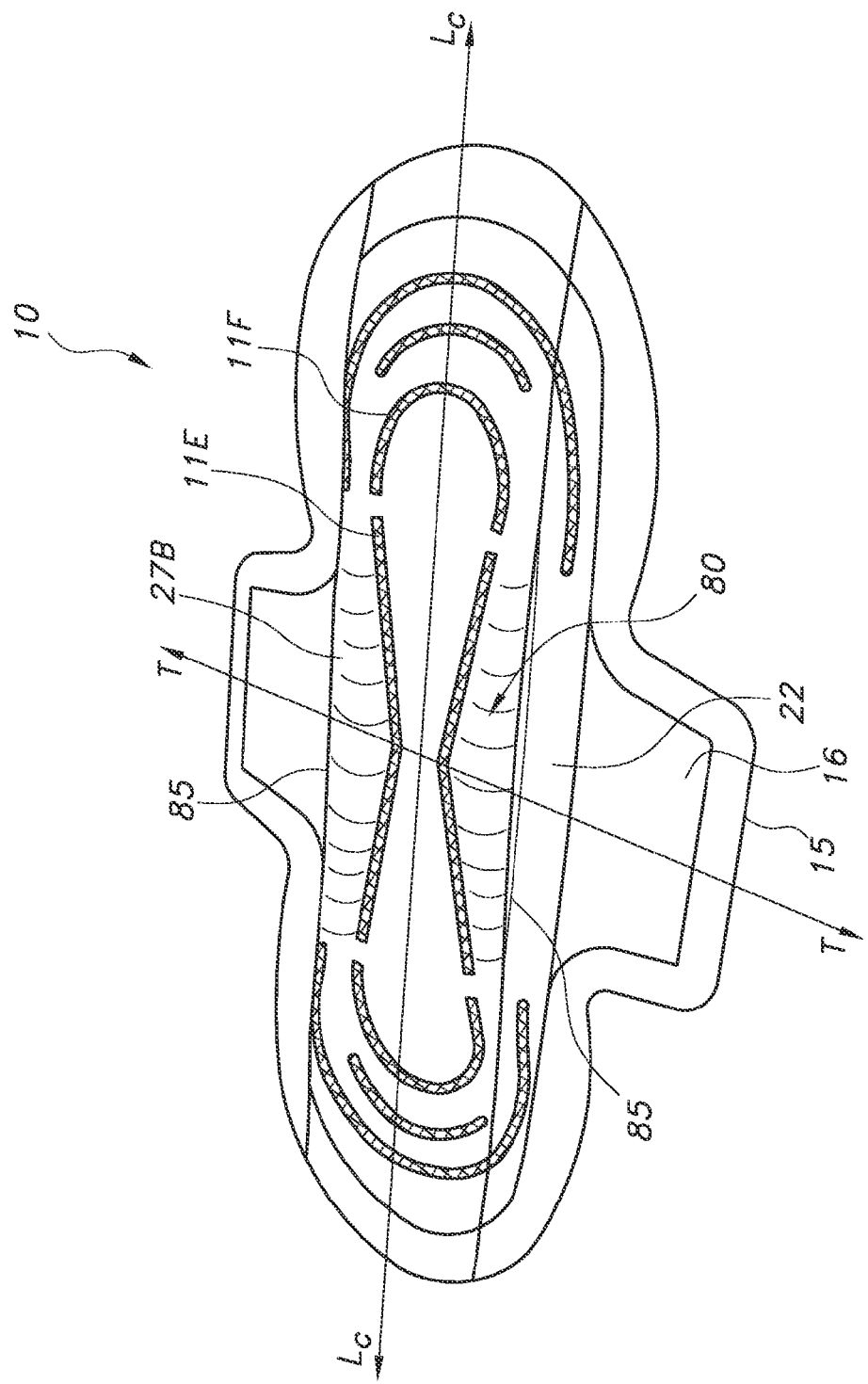
FIG. 1B is a perspective view of still another alternative embodiment of an absorbent article of the invention, in the form of a feminine hygiene pad.
Figure 1C:
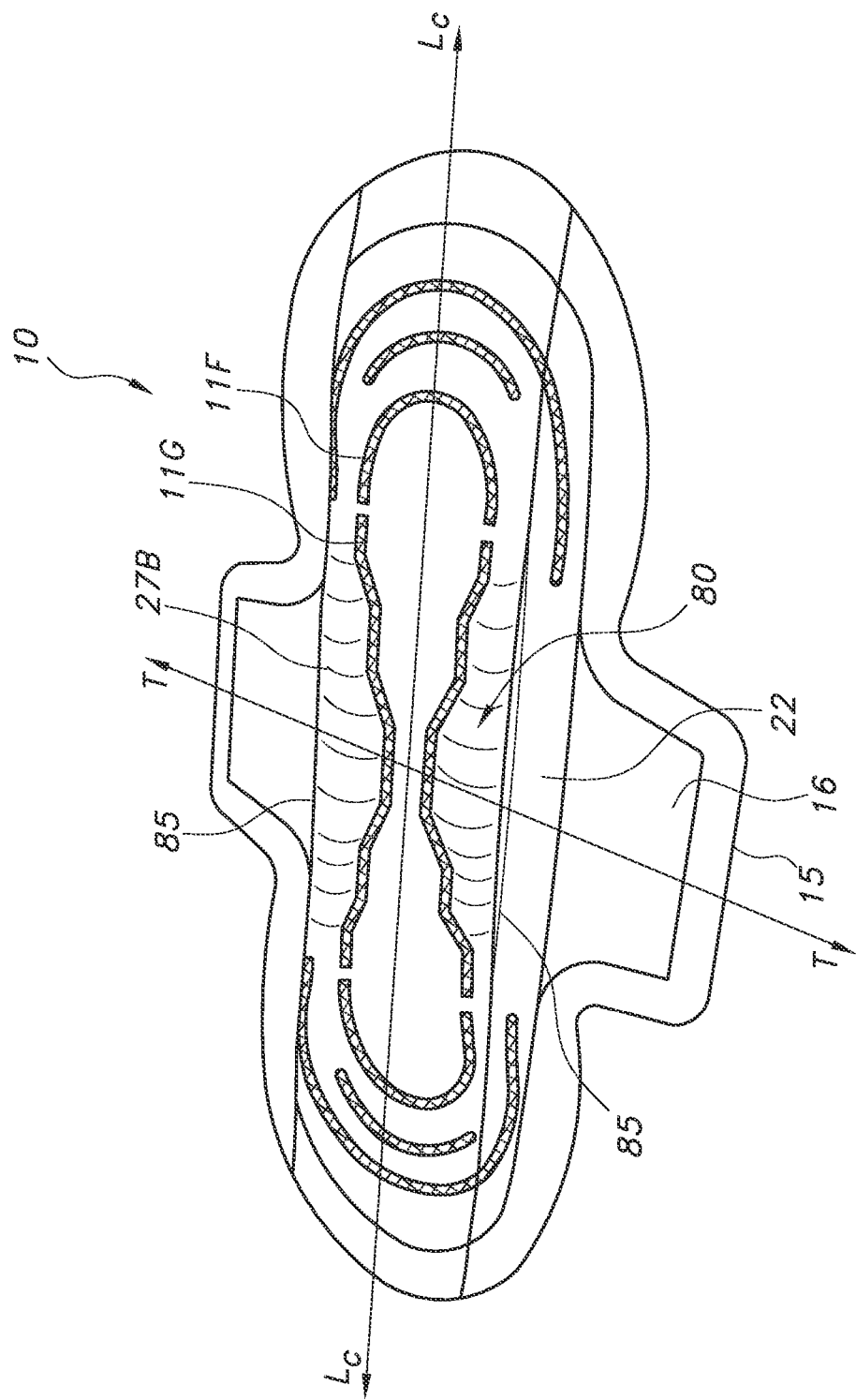
FIG. 1C is a perspective view of yet another alternative embodiment of an absorbent article of the invention, in the form of a feminine hygiene pad.
Figure 9:
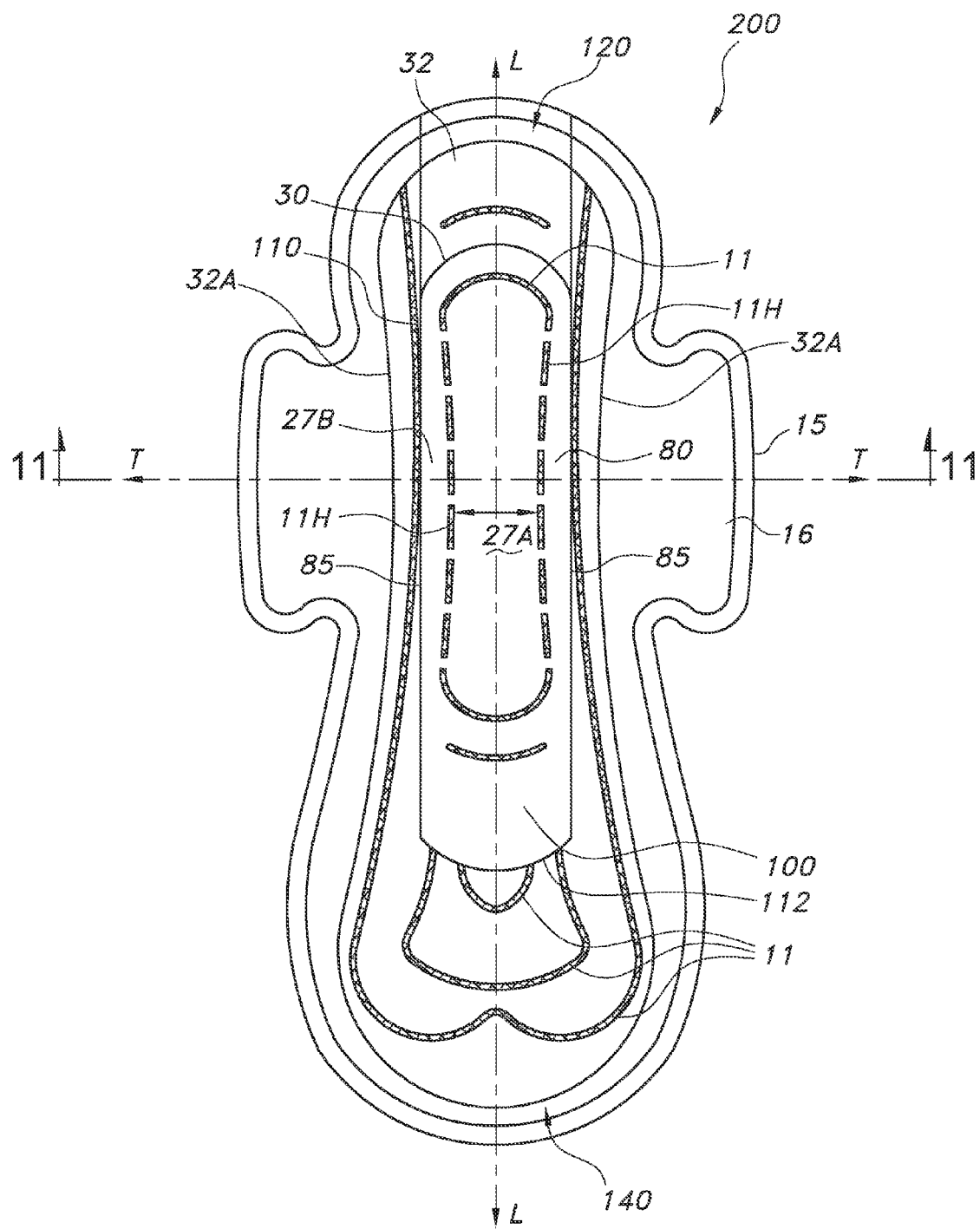
FIG. 9 is a top plan view of an alternative embodiment of the feminine hygiene pad of FIG. 3 in the form of an overnight pad.

Alternatively, such embossed channels can be of an overall indented, or partially indented configuration, such as indented, intersecting straight lines 11E as seen in FIG. 1B, or indented stepped, angular or curvilinear lines 11G as seen in FIG. 1C. Each of the illustrated channels is generally continuous in nature, although they may be separated from the end arc-shaped embossment channels 11B, 11C, and 11F. A wide variety of embossed channels or features are contemplated for use with the invention, although continuous or discontinuous, outwardly concave, curved-shaped channels are preferred (as shown with 11A). Such embossments can be continuous channels having concavities along their length as illustrated in FIGS. 1 (by 11A) and 1A (by 11D) or alternatively, such concave features may be comprised of discrete embossed features or elements that have an overall concave configuration when viewed as a whole along the article longitudinal direction, such as dots, dashes, circles, flowers or other shapes arranged into a concave arc configuration, as seen in FIG. 9 (by 11H).

In specific reference to FIG. 1, the figure illustrates a perspective view of a feminine hygiene pad 10 having absorbent, side barrier features 80, with non-uniform, lateral width dimensions along the side barrier feature length, in accordance with the invention, and also desirably non-uniform height features (H) also along the side barrier feature length. The desirably symmetrically placed, absorbent side barrier features 80 are defined along their transverse direction, by the embossed concave or indented channel 11A on a first side (or the inward side edge closest to the center of the pad and Lc), and a lateral-most edge 85 on a second side (or outward edge closest to the pad longitudinal side edge). As can be seen, the side barrier features 80 are in select portions, elevated and/or not attached at portions (B) to portions of subjacent layers (such as first topsheet layer 22), and are tacked down at select portions of subjacent layers (A,C along their length) at the article longitudinal ends 12, 13. The side barrier features 80, while lying on top of the subjacent layers (and desirably, immediately above a first topsheet layer 22 as will be later described) along the depth direction, are desirably absorbent. The side barrier features are lofty, pillowy features along their detached portions B from the subjacent topsheet layer 22, such as the portion corresponding to the central portion of the pad of FIG. 1. Desirably these are the portions that are immediately adjacent the wings, or other high leakage areas of a pad. The detached portions B need not always be associated with the central portion of the pad however. For example, as seen in FIG. 9, the detached portions adjacent the wings of an overnight pad are more closely associated with one longitudinal end 120 of the overnight pad than the other. Such overnight pad is asymmetrical about the transverse direction. The side barrier features 80 may be part of a larger structure that extends in one embodiment, from one longitudinal end 12 of a pad to the other end 13. Alternatively, they can be discrete structures, extending only a portion of the overall pad length, desirably so long as the largest non-uniform dimensions of the side barrier features 80 with detached lateral-most edge (largest width and/or highest height) correspond in length-wise dimension with, or are adjacent to the lateral side 15 edge areas of the pad that are most likely to encounter leakage. In this fashion, such side barrier features may be applied to regular, super, and extra-long pads. In one embodiment, the lateral-most edge of the side barrier features 85 are inboard (when viewed along the depth direction) of the lateral-most edge of both the article 15, and the first absorbent core layer 32A of the lower pad structure 152. By "inboard", it is meant, closer to the central longitudinal direction Lc than the first absorbent core layer lateral-most edge 32A. As an example, in one embodiment, the transverse width W1 of the second absorbent core layer 30 is desirably smaller than the transverse width W2 of the first absorbent core layer 32. In one embodiment the ratio of the transverse width of the second absorbent core layer to the first absorbent core layer transverse width is between about 0.7 to about 0.9. In another embodiment, such lateral-most edges of the side barrier features 85 are approximately aligned or coextensive with the lateral-most edge of the first absorbent core layer 32A, or a portion thereof, if the first absorbent core layer has non-straight, longitudinal sides. In some instances, it is contemplated that the core layer(s) shape will not be rectangular, but will include rounded side edges.

Figure 3:
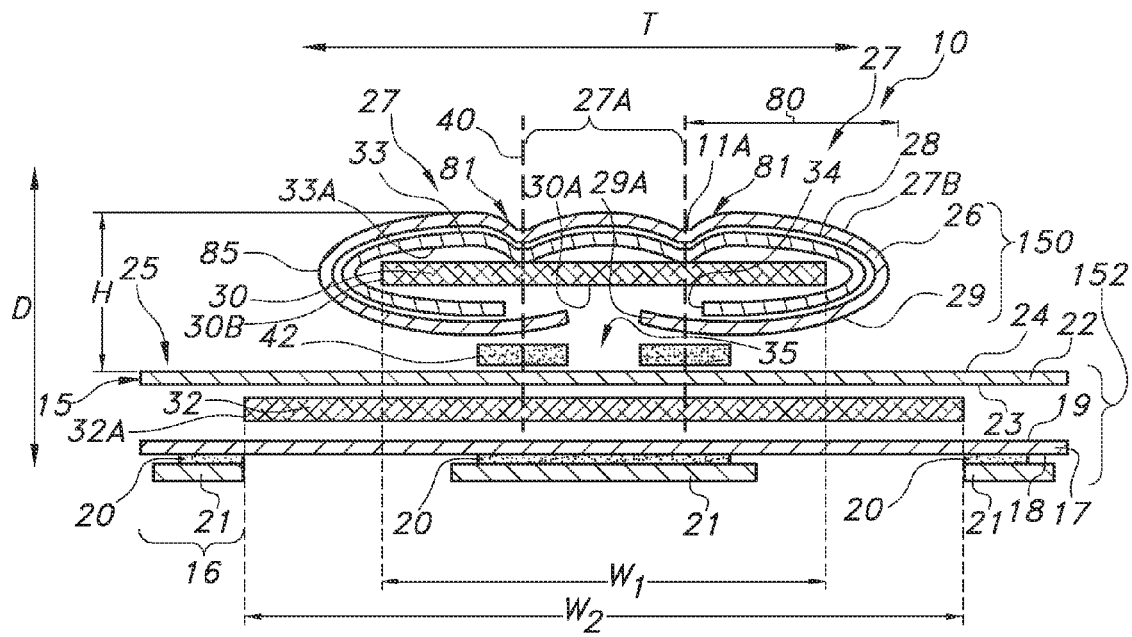
FIG. 3 is an exploded cross-sectional view of the feminine hygiene pad of FIG. 2, taken along line 3-3.

As seen in FIGS. 1 and 3, the second topsheet layer 26, includes a user facing surface 27, in which a central region user facing surface 27A is positioned between the concave embossment channels or embossment features 11A. Desirably a minimum distance of between about 20 and 40 mm separates the concave channels in this central region, alternatively between about 25 and 35 mm. An outer region user facing surface 27B is positioned over the side barrier features 80. The side barrier features 80 desirably include an inclined surface 81 (hereinafter incline) that rises from the concave or indented embossment channels 11A towards the lateral-most side barrier edges 85.

As seen in the figures and in particular, the various exploded cross-sectional views which follow FIG. 1, the side barrier features 80 include the second topsheet layer 26, that is folded about and under, either a subjacent transfer layer 33, an absorbent layer 30, a lofty layer (not shown), or a combination of such layers. These folded layers make up the upper pad structure (also known as upper structure) 150. A concave or indented embossed channel 11A (that is overall concave or indented shape when viewed from the topsheet surface) extends at least through each of these layer along the pad depth direction, at a position 40 inboard of, and in some embodiments, adjacent the lateral-most edge 85 of the side barrier features 80, to thereby create an outwardly directed, desirably raised structure, having an incline 81 towards the side barrier lateral-most edge 85 of the side barrier features 80. Desirably, the concave or indented channel has the widest area of concavity/indentation between the channel and lateral-most edge, adjacent the high leakage areas (wings). Desirably, as will be illustrated below, the embossed channel 11A is embossed through numerous other pad layers in addition to the second topsheet layer 26 and enveloped transfer 33 or absorbent layer(s) 30. In such embodiments, the embossment features are pressed deeply into the pad in the depth direction, such that at least two layers are compressed at the embossed channel positions 40. In one embodiment, the embossed channel 11A extends through at least three layers, including the second topsheet layer 26, a transfer layer 33, and a second absorbent core layer 30. In still a further alternative embodiment, such embossed channels extend in the depth direction through the previously described layers and also the end edges 29A of at least the folded over second topsheet layer 26. In still a further alternative embodiment, the embossed channels extend through the previously described second topsheet layer 26, transfer layer 33 and second absorbent core layer 30, but also through two folded over layers, such as the folded over end edges 29A, (through 34 not shown) of the transfer layer 33 and second topsheet layer 26. In still a further alternative embodiment, such embossed channels extend still deeper into the pad at positions 40 into the lower pad structure 152 (also known as lower structure), such as through the first topsheet layer 22, and/or the first absorbent core layer 32. It has been found that the deeper the embossed channels are placed within the pad layers, the more the incline 81 of the side barrier features 80, resulting in a higher barrier height level H (in the depth direction), at needed high potential leakage areas. See for example FIG. 3. It has also been found that the lateral position of adhesive 42 (if used) holding the upper pad structure 150 to the lower pad structure 152 influences the height (H) of the side barrier features 80. The more lateral the placement of the adhesive 42 along the transverse direction (the closer to the lateral-most side edges 85 of the side barrier features 80), the less height achieved on the side barrier features 80. In one embodiment, the position and/or configuration of adhesive 42 is aligned and coextensive, with the position of the embossment channels 40. For example, such adhesive 42 may not be rectangular in configuration (when viewed in plan view), but instead may be in racetrack or other arc shape, so as to be coextensive with the racetrack or arc shape of the embossment channel 11A.

Figure 2:
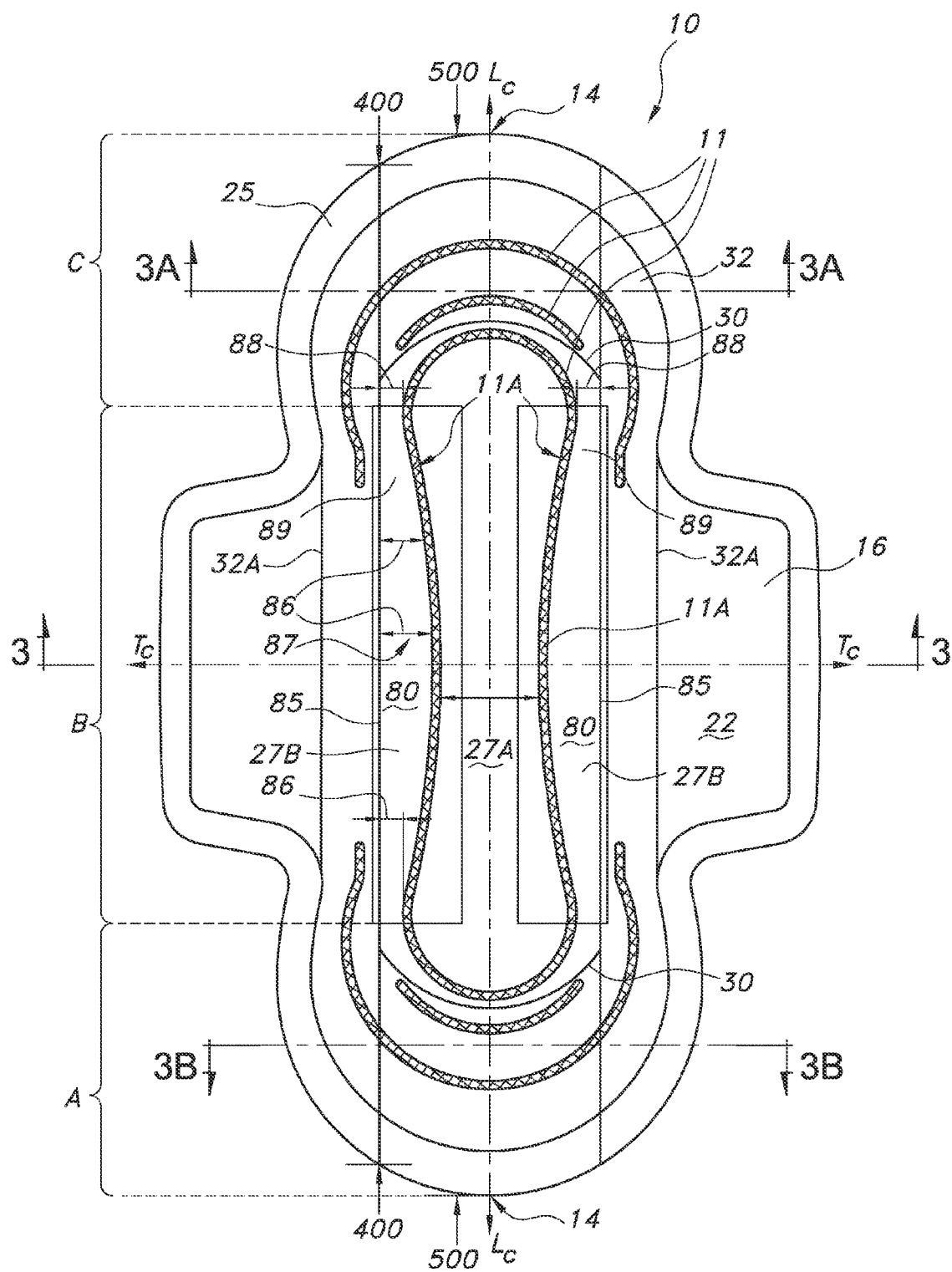
FIG. 2 is a top plan view of the feminine hygiene pad of FIG. 1, highlighting regions or zones containing non-uniform dimensioned barrier features that are not immediately tacked down to subjacent layers.

The side barrier features 80 are desirably, laterally widest (and/or highest along the depth direction) at the portions B immediately adjacent the wings 16, so as to provide the most uninterrupted and targeted area of absorbency (loftiness) between the embossed channel 11A and the opposed side barrier lateral-most edge 85. The width 86 is measured from a point on the embossed channel/feature 11A to the closest point on the opposing lateral-most edge 85. As can be seen in FIGS. 1 and 2, in one desirable embodiment, two side barrier features 80 are desirably positioned symmetrically about the central longitudinal axis Lc, adjacent the lateral sides 15 of the pad. Although two symmetrically positioned and configured side barrier features 80 are shown, it should be understood that in an alternative embodiment, only one of such features may be present in the article. In a further alternative embodiment depending on design preference, such barrier features may not be visually similar adjacent each longitudinal side edges of a pad. Alternatively, depending on the shape of the embossment channel, and tackdown at the article ends, multiple raised or wide barrier features may be present along the same side barrier length. Also, while widest and/or highest side barrier feature portions are shown to be widest and/or highest about and/or adjacent the central transverse direction of the pad in FIGS. 1 and 2, such need not be the case. For example, as seen in FIG. 9, such widest and/or highest side barrier portions 80 of an overnight pad are positioned closer to one longitudinal end 120 of the pad 200 than another 140.

The feminine hygiene pad 10 of FIGS. 1 and 3 also includes a backsheet layer 17, having a garment facing surface 18 and a user facing surface 19. Adhesive patches 20 as are known in the art for attachment of the pad to a user's undergarment, are positioned on the garment facing surface 18 of the backsheet layer 17. Adhesive covers/release sheets 21 as are also known in the art, are placed over the adhesive patches 20 for protecting the adhesive patches prior to use. A first topsheet layer 22 having a garment facing surface 23 and a user-facing surface 24 is desirably sealed to the backsheet layer 17 by a peripheral seal 25. Such peripheral seal may be by any known sealing method such as by adhesive, thermal or ultrasonic bonding methods.

Figure 4:
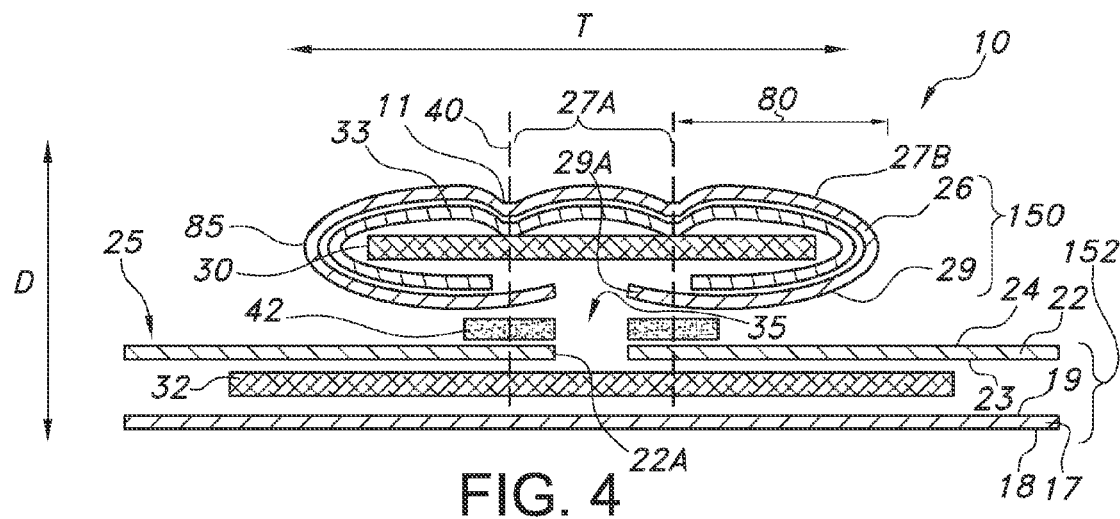
FIG. 4 is an exploded cross-sectional view of an alternative embodiment of the feminine hygiene pad of FIG. 3, taken at approximately the same position along a pad longitudinal direction.
Figure 5:
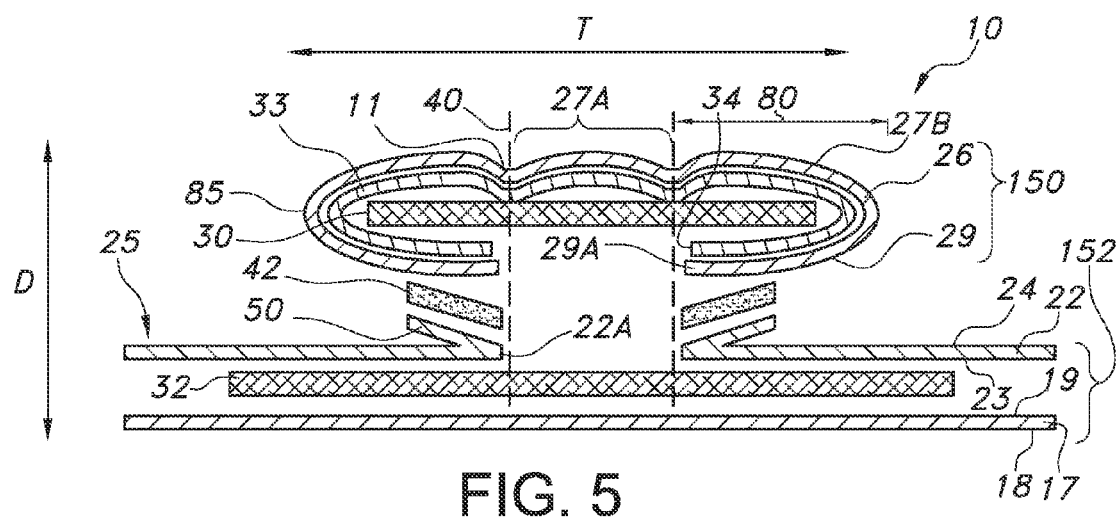
FIG. 5 is an exploded cross-sectional view of another alternative embodiment of the feminine hygiene pad of FIG. 3, taken at approximately the same position along a pad longitudinal direction.
Figure 6:
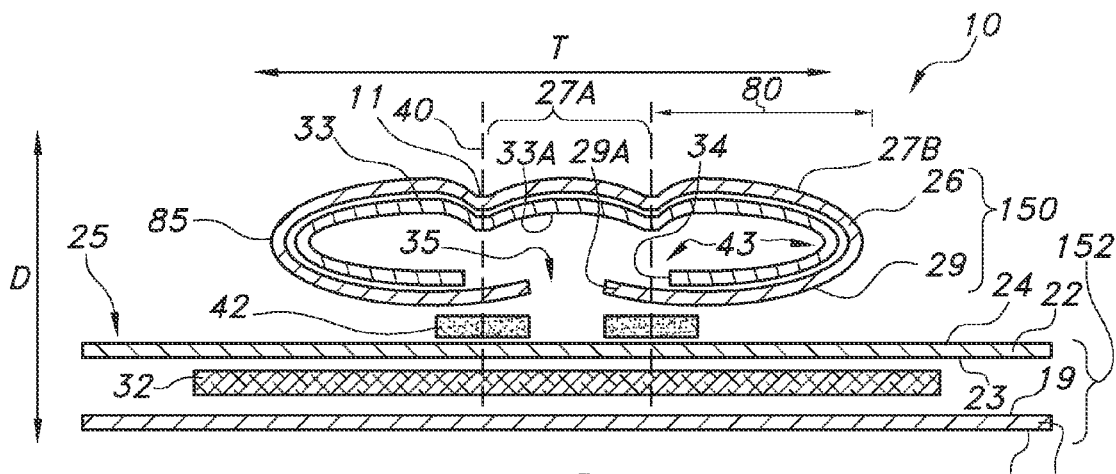
FIG. 6 is an exploded cross-sectional view of another alternative embodiment of the feminine hygiene pad of FIG. 3, taken at approximately the same position along a pad longitudinal direction.
Figure 11:
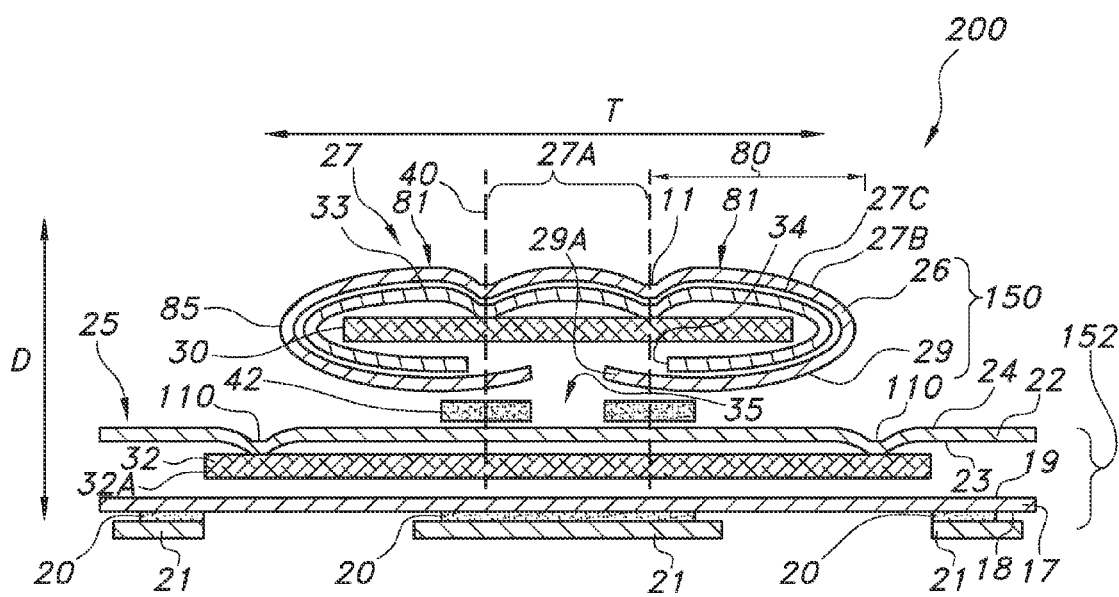
FIG. 11 is an exploded cross-sectional view of the alternative embodiment of the feminine hygiene pad of FIG. 9, taken along line 11-11.

The first topsheet layer 22 may be a continuous topsheet layer which traverses the full transverse direction T of the pad, as shown in the cross-sectional view of FIGS. 3, 6 and 11, or alternatively, may be present in symmetrical discrete sections along the lateral sides of the pad, and may include a separation opening in a central topsheet region defined by first topsheet layer inner ends 22A as illustrated in FIGS. 4, 5, 7, and 8. In still a further alternative embodiment, the first topsheet layer may be present only along the periphery of the pad, such as at the same general location as the first topsheet layer 22 of FIG. 4 but in a configuration that defines a completely surrounded central opening (such as the top plan view of an elongated donut), not including distinct and separated longitudinally directed lateral sections. Such alternative is not shown in the figures. Such first topsheet layer 22, if a continuous topsheet layer, may itself be manufactured from two different materials across its transverse direction, with a central longitudinally directed strip of a first cover material and two longitudinally directed side covers of a second material. Such dual layer topsheet configuration offers the benefit of having a desired first material at one location along the topsheet surface, such as for example a softer side material for contact with a user, and a second material only along the central longitudinal direction of the pad, such as a more "open" material for fluid to permeate into a subjacent absorbent layer. In any event, such first topsheet layer 22 and backsheet layer 17 sandwich a first absorbent core layer 32, essentially sealing it between the two layers by the peripheral seal 25.

A second topsheet layer 26, situated above and adjacent the first topsheet layer 22 along the depth direction, includes a second topsheet layer user facing, surface 27, having a central region user facing surface 27A between embossed concave channels 11A, and user facing outer region surfaces 27B. The second topsheet 26 layer includes a garment facing surface 28, and a folded-under portion 29, terminating in folded-under ends 29A. The second topsheet layer 26 is wrapped about either a second absorbent core layer 30 (having a user-facing surface and garment-facing surface 30A), a fluid transfer layer 33 (having a garment-facing surface 33A), other lofty layer (not shown), or a combination of such layers. As seen in FIG. 1, the second topsheet layer 26 is folded about (and with) a transfer layer 33, which combination of layers are together folded about the lateral-most side edges 30B of a second absorbent core layer 30. While the fluid transfer layer 33 desirably itself also at least partially envelops the second absorbent core layer 30 as shown and terminates in fluid transfer layer folded-under ends 34, it need not envelop such second core layer. The second topsheet layer 26 is wrapped about the transfer layer 33 and second absorbent core layer 30 by being folded around (in the depth direction) the transfer layer 33 and second absorbent core layer 30 and ending in the folded-under ends 29A. The folded layers in one embodiment, desirably do not completely encircle the transfer layer 33 and/or second absorbent core layer 30 as the case may be. In this fashion, an internal fluid communication channel 35 is created through the opening between the second topsheet layer 26, folded-under ends 29A, the opening between the fluid transfer layer folded-under ends 34, and the first topsheet layer inner ends 22A, if present (See FIG. 4). Such internal channel 35 leads either to the first absorbent core layer 32 or the first topsheet layer 22, depending on the embodiment. The internal channel serves as a fluid communication pathway through the interior of the pad from the upper layer structure 150 to the lower layer structure 152 in the depth direction. As seen in FIG. 3, the combination of the second topsheet layer 26, transfer layer 33 and/or second absorbent core layer 30 form the upper pad structure 150, which itself forms the side barrier features 80 via the embossment channels 11A and longitudinal end tackdowns described below.

The embossed channels 11A, with two concave or indented embossment features along the pad longitudinal direction, are situated on the pad user-facing surface, and extend through one or more subjacent layers, at a location 40 that is a desired distance 86 from the side barrier feature lateral-most edge 85. As can be seen in FIGS. 1 and 1A, the curvature/loftiness of the side barrier features 80 may vary by design. For example, the side barrier features 80 may be more pronounced in one embodiment (as seen in FIG. 1), as defined by the basis weight/properties of layers within the upper pad structure 150 and the embossing channel design (and placement). Such pronounced side barrier features 80 may appear more significantly elevated above subjacent layers (22) in select portions (B). For example, in one embodiment, the height (H) range of the side barrier feature 80 at a position adjacent or including its laterally widest location 87 of portion B, may be between about 1 and 12 mm, desirably between about 4 and 10 mm, more desirably between about 4 and 8 mm, still more desirably about 6 mm. For the purposes of this application the height (H) is the measurement between the highest vertical point of the side barrier feature 80 (along the depth direction) to the first topsheet layer 22, as measured when the pad/article is in a flat and open, non-compressed state (as illustrated in FIG. 2). In one embodiment, the height range of the side barrier feature 80 at, or adjacent the laterally widest location (such as 87) may be between about 6 and 10 mm. Desirably, in one embodiment, the height ratio of the highest point height at portion B to an end portion height (A or C), of the upper structure is about 5:1. In one embodiment, the height ratio range is between about 12:1 to 1:1, from highest to lowest points along the side barrier feature length (along the article length). Alternatively, it is between about 5:1 to 1:1. The height can be impacted by the thickness of the upper structure layers, the embossing curvature, and the placement and configuration of adhesive or other bonding means holding the upper pad structure to the lower pad structure. The end portions (portions A and C) of the upper structure 150 in which the side barrier features are not detached from the subjacent layers at the lateral-most edge 85, may run to the product ends or to a position short of the product ends. See in this regard FIGS. 1, 1A and 2. Alternatively, the side barrier features 80 may be less pronounced as seen in FIG. 1A, and appear less significantly elevated above subjacent layers (22) in select portions (B).

As seen in the top plan view of FIG. 2, the lateral-most edges 85 of the side barriers 80 are desirably straight or substantially straight in configuration. This is in contrast to the concave embossment channel 11A forming the other side of the side barrier features 80. Together these features define the structure forming an absorbent barrier feature, akin to a wall closest to the pad side edge 15. For the portion B of the side barrier feature 80 lateral-most edge 85, along the longitudinal direction which is adjacent the concave or indented portion of the embossment channel 11A, the side barrier is not tacked down or otherwise bonded to the subjacent layer 22 at its lateral-most edge 85. This portion B is further illustrated by the outlined box 89 shown in FIG. 2 which highlights desired areas of the side barrier features 80 which are not tacked down to a subjacent layer 22 along the lateral-most side edge 85. This box is presented merely to facilitate understanding of this portion. Such "visualization" box 89 would not necessarily be present on the actual pad, as seen by the consumer. However, it is contemplated in one embodiment, that such detached side barrier feature 80 portions (B) could be visually distinguished in some fashion from the rest of the pad for the consumer, such as by printing or the inclusion of other visually distinguishing elements. The entire lateral-most edge 85 of the side barrier portion contained within this box, or a smaller edge portion thereof, may be unconnected to the subjacent layer. Portions of the side barrier features 80 outside of this imaginary box, such as portions A and C are desirably tacked down or otherwise bonded to the subjacent first topsheet layer 22, such as by embossment channels 11 which extend close to the lateral-most edge 85 (of a larger upper pad structure in portions A and C) or adhesive. As a result of the concave embossment channel 11A, the lateral width 86 of the side barrier 80 non-tacked down portion B, varies along the length direction of the pad, with a larger or largest widths 87, being desirably positioned towards the center of the pad, adjacent the wings 16, and desirably along a central transverse axis Tc. Depending on the embossed channel configuration, the largest width may be positioned at another location along the longitudinal direction of the pad, but desirably adjacent a wing, as seen in FIG. 9. Desirably, for the embossment channels, such as that shown in FIG. 2, the width measurement between the embossment feature and lateral-most side edge 85 is narrowest in the tacked down end regions A, C, as shown at 88. This is desirable whether or not the embossment channel is a continuous or discontinuous channel/feature. By including the embossment channel or feature close to, on top of, or crossing over the lateral-most side edge of the barrier feature 80, it is possible to tack down the lateral-most edge to a subjacent layer with the embossment channel if desired. In this fashion, a simplified process without extra adhesive may be used to create the "free or detached edge"-containing barrier feature.

In one embodiment, the maximum or widest width ranges 87 (distance between a point on the channel 11A and the closest point on the opposed lateral-most edge 85) of the side barrier feature 80 is between about 4 and 12 mm, in one embodiment between about 4 and 9 mm, in a further embodiment, between about 4 and 6 mm. In an alternative embodiment, the maximum width is between about 7 and 12 mm. In yet another alternative embodiment, the maximum width is between about 7 and 9 mm. In one embodiment, the minimum width of the side barrier between the lateral-most edge 85 and the channel 11A where a concave feature ends 88 (by becoming either straight, convex in configuration, or ending) is between about 0 and 8 mm. Alternatively, the minimum width of the side barrier feature is between about 0 and 6 mm. Still in a further alternative embodiment, the minimum width is in the range of greater than 0 to about 6 mm, still alternatively between about 1 and 2 mm. In still a further alternative embodiment, the ratio of the maximum lateral width to the minimum lateral width of the side barrier feature 80 is about 12:1. In another embodiment, a ratio range of the maximum lateral width to the minimum lateral width (that is the untacked lateral-most side edge 85 portion B) is between about 12:1 to >1:1.

It should be recognized that the upper pad structure may extend the whole length of the pad, or some smaller length along the pad. Desirably the upper pad structure which includes the tacked and untacked portions (A,B,C) extends a substantial length of the overall pad, such as in one embodiment, between about 40 and 100 percent, alternatively between about 80 and 90 percent. Desirably, the untacked portion of the side barrier feature 80 extends a substantial portion of the overall upper structure length, and overall pad length, such as in one embodiment between about 30 and 100 percent of the structure (alternatively between 40 and 60 percent of the structure) or between about 20 and 80 percent of the overall pad length (500), alternatively between about 30 and 60 percent. (See FIG. 2). In some instances for rounded-end pads, the upper structure including the side barrier feature may have at least two different lengths (400, 500) across the pad transverse direction, based on the outer shape of the pad. In one embodiment, that portion of the side barrier feature 80 which is not tacked down along its lateral-most edge 85 is between about 70 and 200 mm, alternatively, between about 110 and 130 mm.

In a further alternative embodiment, those total portions of upper pad structure which are tacked down along the lateral-most edge 85 to a subjacent layer (portions A and C) are between about 20 and 800% of the overall pad length, alternatively between about 40 and 70% of the total pad length (500). In yet a further alternative embodiment, those total portions of the side barrier feature 80 which are tacked down to a subjacent layer (portions A and C) along the lateral-most edges 85 are between about 0 and 70% of the side barrier feature containing-structure length, or alternatively, between about 40 and 60%. In yet a further alternative embodiment, those portions of the side barrier features 80 which are tacked down along the lateral-most edge 85 are not equal at each longitudinal end of the pad, and in still a further alternative, total between about 0 and 100 mm (that is a number greater than 0 to about 100 mm). Alternatively, the tacked down portions range from 70 to 90 mm in total length. The width and length dimensions present in this description may be higher or lower depending on whether the pad is a regular (or normal flow), super, or extra-large (overnight or heavy flow) pad.

In still a further alternative embodiment, the total basis weight of the layer or layers contained in the upper structure 150 of the pad, excluding the second topsheet layer, is between about 18 and 350 gsm. This basis weight total may, in one embodiment, include the basis weight of any adhesive in the upper pad structure. Alternatively, the basis weight of the layer or layers contained in the upper structure 150 of the pad, excluding the second topsheet layer, is between about 200 and 250 gsm. In one embodiment, the length of the transfer layer 33 (parallel to Lc) if present, is approximately the same as the second topsheet layer 26. In a second embodiment, the length of the transfer layer if present, is less than that of the second topsheet layer 26. In a further embodiment, the length of the second absorbent core layer 30 is approximately the same as the length of the second topsheet layer 26 and/or the transfer layer 33. Alternatively, the length of the second absorbent core layer 30 is less than that of the second topsheet layer and/or transfer layer, such as between about 20 and 90% of the pad length, or alternatively between about 40 and 70% of the pad length (or still, alternatively, between about 90 and 200 mm, alternatively between about 110 and 150 mm). In still a further alternative embodiment, the length of the second absorbent core layer 30 is less than that of the first absorbent core layer 32, such as between about 30 and 90% of the first absorbent core layer 32, alternatively between about 50 and 80% of the first absorbent core layer 32. In one particular embodiment, the length of the pad 500 is between about 230 and 240 mm (for regular size pads), the length of the non-tacked down side barrier portion B is between about 120 and 150 mm, the length of the first absorbent core layer is between about 200 and 210 mm, and the length of the second absorbent core layer is between about 120 and 150 mm. In one embodiment, the transverse width of the second absorbent core layer 30 (W1) is less than or equal to the transverse width (W2) of the first absorbent core layer 32.

As seen in FIG. 3, which illustrates an exploded, cross-sectional view of the feminine hygiene pad of FIG. 2 taken along line 3-3 in the wing area, the side barrier features 80 are formed from the upper pad structure 150 which is tacked at the folded lower topsheet surface 29, either by adhesive 42 or other bonding means to the first topsheet layer 22 user-facing surface 24 (of the lower pad structure 152). Such bonding is desirably symmetrically about the central longitudinal direction (axis Lc). Other bonding means may be by thermal or ultrasonic bonding techniques. Such bonding may be continuous or discontinuous (at least along the longitudinal direction of the pad), such as for example by adhesive stripes which extend the full length of the pad, and optionally across the transverse direction, especially where there is complete tackdown of the side barrier features 80 (at portions A and C). Alternatively, such bonding may be discontinuous, such as by discontinuous stripes of adhesive, either along the longitudinal direction and/or transverse directions where appropriate.

The height H of the upper pad structure 150 may in one embodiment, vary along the side barrier feature 80 length, with the largest height dimension desirably present in or adjacent the wing area (as in portion B). Therefore, in one embodiment, the side barrier feature 80 demonstrates a varying width along its length. In a second embodiment, the side barrier feature or features 80, demonstrates a varying height along its length. In a third embodiment, the side barrier feature or features demonstrates both a varying width and height along its length (along the pad longitudinal direction). The varying width and height are the result of both the tackdown of the side barrier feature along different portions of the pad length, as well as the placement of the embossment channel concavities/indentations along or adjacent the feature length.

Figure 7:
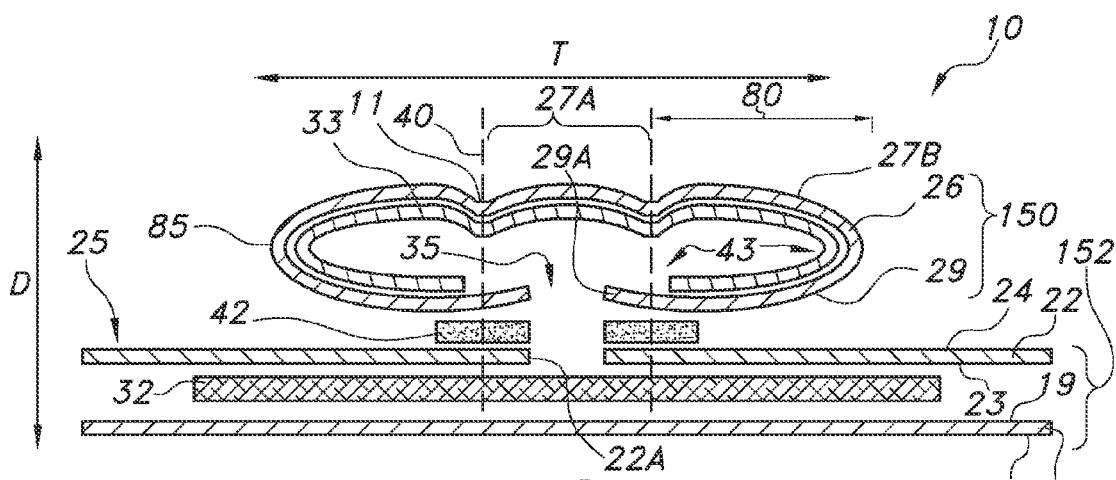
FIG. 7 is an exploded cross-sectional view of another alternative embodiment of the feminine hygiene pad of FIG. 3, taken at approximately the same position along a pad longitudinal direction.
Figure 8:
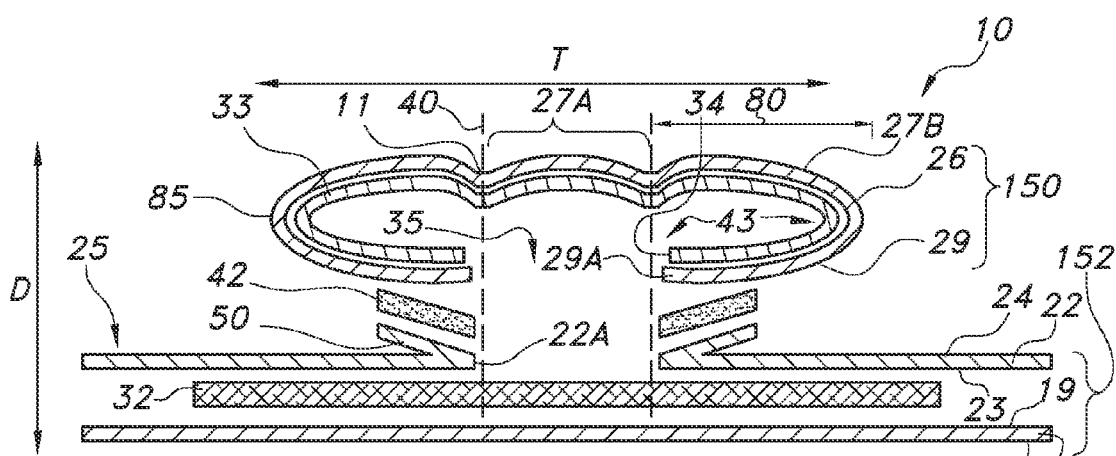
FIG. 8 is an exploded cross-sectional view of still another alternative embodiment of the feminine hygiene pad of FIG. 3, taken at approximately the same position along a pad longitudinal direction.

The second topsheet layer 26, either alone or in conjunction with a transfer layer 33, is desirably partially folded along the depth direction such that the ends 29A and 34 of the second topsheet layer 26 and transfer layer 33 (if present) wrap about a void space 43 (as seen in FIGS. 6, 7 and 8), or alternatively, the lateral edges 30B of a second absorbent core layer 30 (as seen in FIGS. 3, 4, and 5). The wrapped second topsheet layer 26 and transfer layer 33 may be approximately coextensive along the transverse direction, such as shown in FIGS. 5 and 8, or non-coextensive, as illustrated in the other cross-sectional views. Concave or indented embossing channels or other features, as shown in 11A, 11D, 11F, 11G (concave or indented with respect to the lateral side edges of the pad 15) are placed on the user facing surface 27 of the second topsheet layer and penetrate at locations 40 such that they compress two or more layers of the pad. Essentially, the embossment channels or embossment features extend downwardly (along the depth direction of the article), through two or more layers within the article.

Figure 3A:
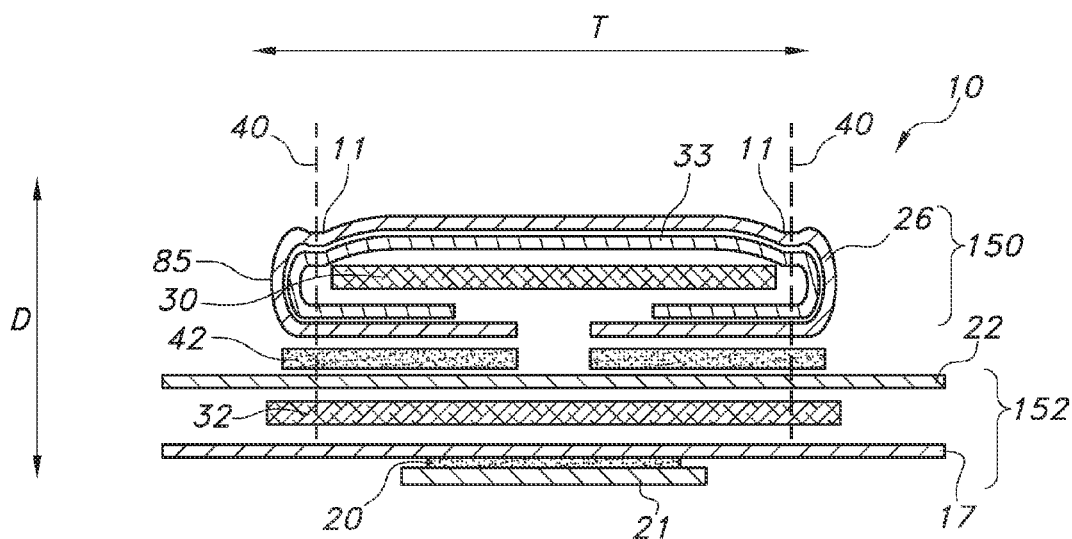
FIG. 3A is an exploded cross-sectional view of the feminine hygiene pad of FIG. 2, taken along lines 3A-3A (and lines 3B-3B, which is a mirror image of line 3A-3A).

As seen in the exploded cross-sectional view of FIG. 3A, taken along line 3A-3A of FIG. 2, the upper pad structure 150 is fully tacked down to the subjacent layer (the first topsheet layer 22) of the lower pad structure 152 in portion C (and A). In this portion, there is desirably little-to-no free lateral-most barrier edge 85, as the structure is bonded by the embossing channel 11 at or immediately adjacent the lateral-most edge 85, which tacks this edge down to a subjacent layer (such as 22). Alternatively, as shown in the figure, the adhesive layer 42 may optionally extend further along the transverse direction, only in this end region (portions A and C) to further tack the upper and lower pad structures together. Other known bonding techniques are also contemplated for use in these portions A and C to achieve this tackdown. In the tacked down portions (A and C) of the pads, there is desirably little-to-no physical separation space (along the continuous lateral-most edge 85) between the upper structure and the lower structure.

An exploded, cross-sectional view (at approximately the same transverse direction/location near a pad's wings) of an alternative feminine hygiene pad embodiment is illustrated in FIG. 4. Whereas FIG. 3 illustrates a first topsheet layer 22 which continuously traverses the pad transverse direction, FIG. 4 illustrates a non-continuous first topsheet layer 22 having first topsheet layer inner ends 22A. In the embodiment of FIG. 4, the channel 35 between the upper pad structure 150 and the lower pad structure 152 provides direct fluid communication to the first absorbent core layer 32 from the second absorbent core layer 30. Adhesive 42 bonds the second topsheet layer ends 29A to the inner ends 22A of the first topsheet layer 22, without blocking the fluid communication channel 35. The exploded cross-sectional view (taken at approximately the same position) of still a further alternative feminine hygiene pad is illustrated in FIG. 5. As seen in this figure, the second topsheet layer 26 and transfer layer 33 are approximately coextensive, having ends 29A, 34 which terminate at approximately the same location in the transverse direction (but along different depth direction planes). In this alternative embodiment, rather than being separated single planar strips as seen in FIG. 4, the separated first topsheet layer 22 strips include folded inner ends 50, which folded inner ends extend outward from the center of the pad towards the side barrier feature lateral-most edges 85. Such folds provide additional bulk which enhances the lofty nature of the side barrier features 80. Additional advantages of the folded inner ends of the first topsheet layer include increased fluid communication channels between the absorbent materials of the upper pad structure and the absorbent materials of the lower pad structure. In such embodiment in FIG. 5, the position of the embossment channels 40 is located such that they do not compress the folded inner ends 50, but are more inwardly situated along the pad transverse direction (more towards Lc), compressing the first absorbent core layer 32. The folded inner ends 50 are outwardly directed away from the central longitudinal direction Lc. Alternatively, the embossment channels may hit the folds, depending on the intended width of the side barrier features.

An exploded cross-sectional view of still a further alternative embodiment of a feminine hygiene pad is illustrated in FIG. 6, taken again, at approximately the same transverse direction near the wing locations. As seen in the figure, there is no second absorbent core layer adjacent the garment facing surface 33A of the transfer layer 33 present in the upper pad structure 150. Rather, the second topsheet layer 26 and transfer layer 33 are folded together in the depth direction with the ends of the second topsheet layer 29A extending further than the ends of the transfer layer 34 towards the central longitudinal direction of the pad. The folded layers surround a void 43, which is actually compressed such that the inner surfaces of the surrounding layers touch (but shown otherwise in the exploded view). The figure also illustrates a continuous, transversely directed first topsheet layer 22 through which body fluid travels after it leaves the upper pad structure 150. The embossment 11 position 40 is shown through the second topsheet layer 26 in two vertically separated locations, as well as through the transfer layer 33 in one location, the first topsheet layer 22 and the first absorbent core layer 32.

An exploded cross-sectional view of still a further alternative embodiment of a feminine hygiene pad is illustrated in FIG. 7, taken again, at approximately the same transverse direction near the wing locations. The figure illustrates a separated first topsheet layer 22 having inner ends 22A. The embossment 11 position 40 is shown through the second topsheet layer 26 in two vertically separated locations, as well as through the transfer layer 33 in one location, the first topsheet layer separated inner ends 22A and the first absorbent core layer 32.

An exploded, cross-sectional view of still a further alternative embodiment of a feminine hygiene pad is illustrated in FIG. 8, taken again, at approximately the same transverse direction near the wing locations. The figure illustrates a separated first topsheet layer 22 with folded inner ends 50. The embossment 11 position 40 is shown through the second topsheet layer 26 in one location, as well as through the transfer layer 33 and the first absorbent core layer 32.

Figure 10:
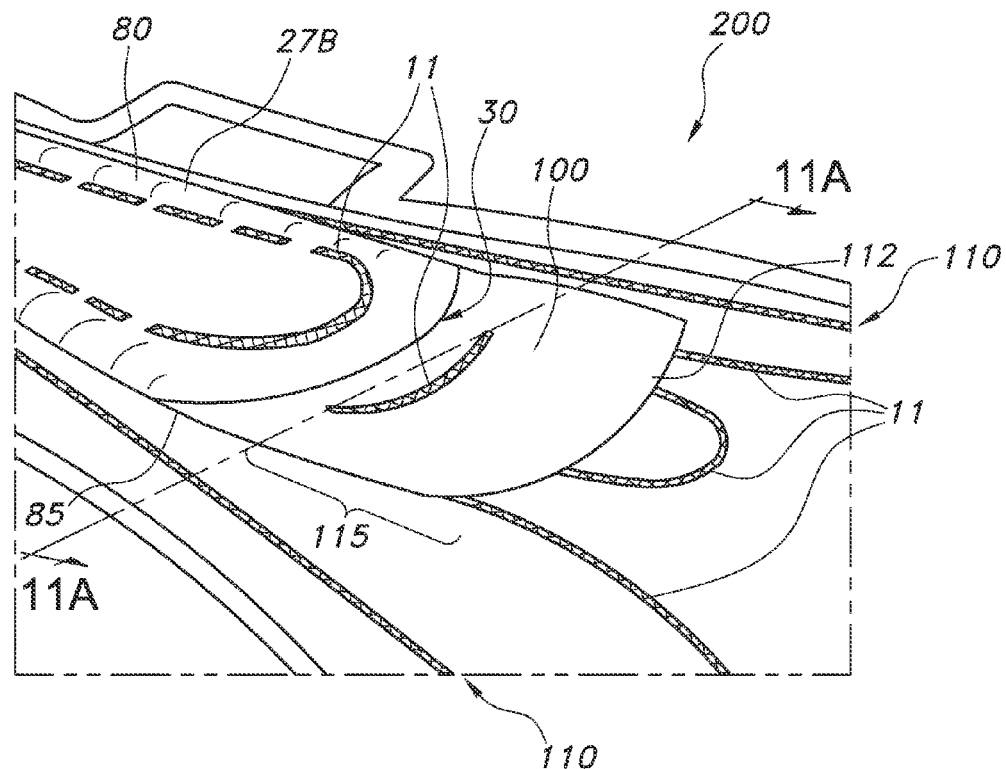
FIG. 10 is a partial top perspective view of a portion of the overnight pad of FIG. 9.
Figure 11A:
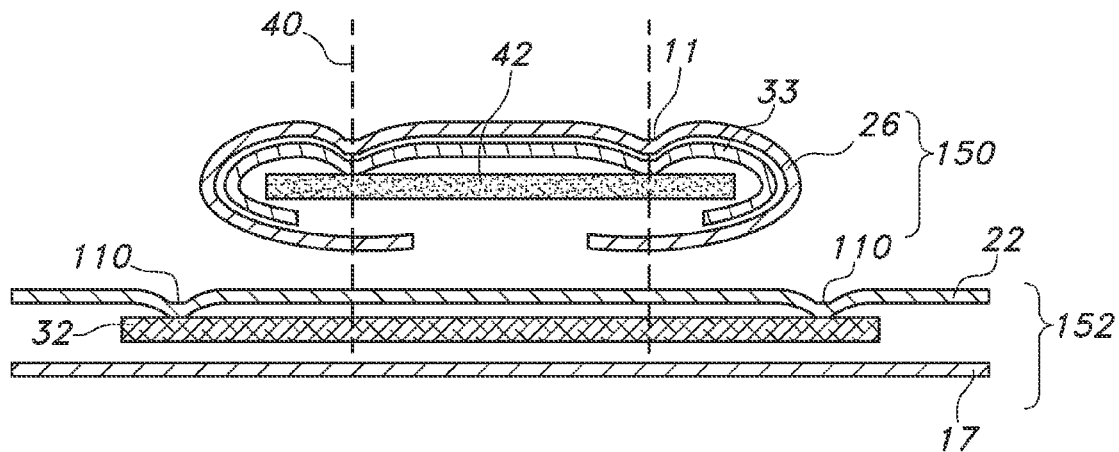
FIG. 11A is a partial exploded cross-sectional view of the alternative embodiment of FIG. 9, taken along line 11A-11A off of FIG. 10 in the overhanging tail-like region.

As previously noted, an alternative embodiment of the feminine hygiene pad of FIG. 1 is shown in FIG. 9 in the form of an overnight feminine hygiene pad 200. Overnight pads are often used by consumers during overnight sleeping hours or during heavy menstrual flow days. As illustrated in the figure, such overnight pads include asymmetrical shapes in which a first end 120 includes an outer shape different from a second end 140. In the case of the illustrated embodiment, the overnight pad 200 includes an upper pad structure (as seen in FIGS. 10,11, and 11A) that does not run the full length of the overall pad. Rather, the upper pad structure 150 includes both side barrier features 80 that are 1) tacked at one end of the article, 2) untacked to subjacent layers along the lateral-most side edge 85, and 3) untacked at a longitudinal end 100 terminating in a back end edge 112 which is also untacked to subjacent layers at a region 115 rearward, such as at positions rearward of an arc-shaped embossment channel 11. The small arc-shaped embossment channel 11 acts to hold the beginning of the tail region down to the subjacent layer(s). In such untacked, overhanging, tail-like region 115, it is desirable for such upper pad structure to be free of a second absorbent core layer in the overhanging tail, and only include a second topsheet layer and a transfer layer in this tail-like region. A layer of adhesive holds the layers within the upper pad structure 150 in that region 115 together, but not the tail itself to the subjacent first topsheet layer 22. In such an embodiment, a second absorbent core layer may or may not be present in the upper pad structure 150, closer to a first end 120. Additional embossment channels 110 are desirably situated more laterally than the lateral-most edges 85 of the side barrier features 80. Such additional embossment channels 110 are situated on the first topsheet layer 22 and optionally, subjacent layers of the lower pad structure 152 in the depth direction of the pad 200. In alternative embodiments, elastic and/or shrinkable fibers or yarns may be positioned within or adjacent the second topsheet layer 26, such as along the second topsheet layer tail-like extension 115, so as to maintain the tail in an elevated position upon soiling.

As noted for pads, such as for example overnight pads and extra-long pads/articles, the tackdown region(s) A and C for an upper structure which includes the side barrier features 80 along their length, may be 1) at both the ends of the article if the upper structure runs the full length of the pad, 2) only at one end and also at a central location along the pad length, or 3) at positions substantially inboard of the pad outer edges, more towards the center of the pad (especially if the side barrier features are short, discrete structures not part of larger upper structures that run the full length of the pad).

Figure 12:
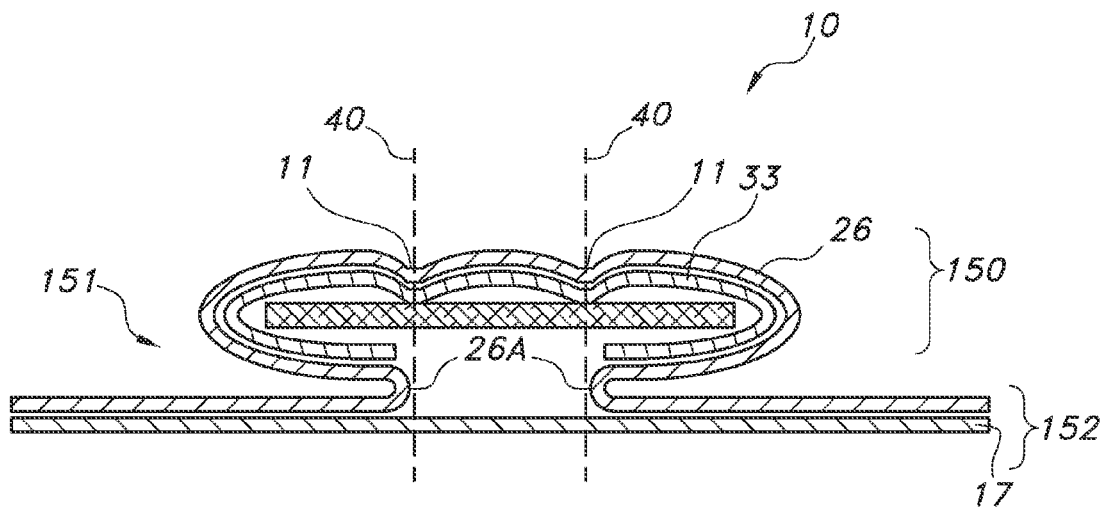
FIG. 12 is an exploded cross-sectional view of an alternative embodiment of the feminine hygiene pad of FIG. 3, taken at approximately the same location along the longitudinal direction of a pad adjacent the wings.

In still other alternative embodiments, the second topsheet layer 26 and other folded layers of the upper structure 150 may completely envelop either a void space or absorbent core layer, or alternatively be folded in an "S" or reverse "S" configuration 151 along the transverse direction so as to also become the first topsheet layer when folded towards the lateral side edges into the lower structure 152, as seen in FIG. 12. The actual folds of the second topsheet layer 26A may be positioned away from the position of the embossment channels 11 towards the lateral side edges of the product (as shown), or alternatively, may be positioned within the path of the embossment channel(s) so as to be embossed with the upper structure layers. If the second topsheet layer 26 completely envelops the upper absorbent layers (not shown) the lower portions of the second topsheet layer 26, may be apertured to allow for more rapid fluid communication to the lower pad structure 152 if such lower pad structure includes a first absorbent core layer. Such lower pad structure, may alternatively not include a first absorbent core layer structure, as seen in FIG. 12.

Figure 13:
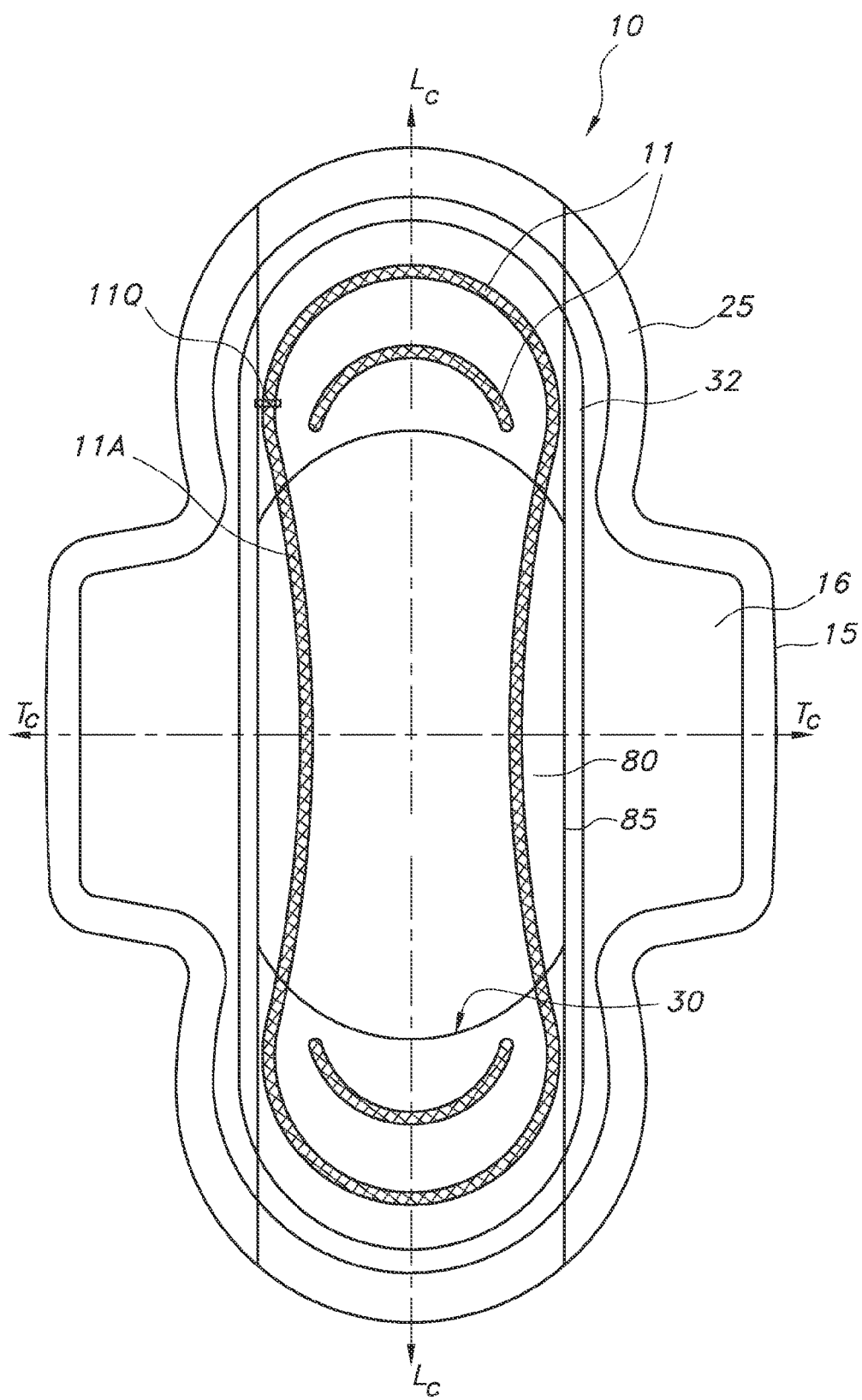
FIG. 13 is an alternative embodiment of the feminine hygiene pad of FIG. 1, in which the embossment channel is continuous adjacent the periphery of the pad.

In still another alternative embodiment of the feminine hygiene pad 10 in FIG. 13, a pad includes a continuous embossment channel 11 adjacent the periphery of the pad, and specifically over the absorbent layers 30, 32. As seen in the figure, the embossment channel concave portions 11A along the longitudinal direction of the pad provide an inward side edge, that together with the lateral-most edge 85 defines the raised portion of the side barrier features adjacent the pad wings 16. The embossment channel 11 is positioned such that it approaches the edge of the pad on all sides 11Q, towards the longitudinal ends, such that the larger structure including the side barrier features are tacked down, at least by these side embossment features 11Q. Additional adhesive may also be placed under the topsheet layer for additional tackdown in these areas.

Materials for Use in the Various Layers of the Pad/Absorbent Article Structure

The first and second topsheet layers may each be of a single layer material, or alternatively, of multiple layers that have been laminated. Such first and second topsheet layer materials may be formed from numerous materials known in the art, such as for example, one or more fibrous nonwoven sheets, one or more film sheets, such as blown or extruded films, which may themselves be of single or multiple layers, one or more foam sheets, such as reticulated, open cell or closed cell foams, one or more woven sheets, a coated nonwoven sheet, or a combination of any of these aforementioned materials. Such combination may be adhesively, thermally or ultrasonically laminated into a unified planar sheet structure.

The first and second topsheet layers function to receive and take in fluids, such as urine or menses, and therefore comprise a liquid permeable material as noted. Additionally, the first and second topsheet layer materials can further function to help isolate the wearer's skin from fluids held in a subjacent absorbent layer of an absorbent article. One or more chemical treatments can be applied to either or both of the first and second topsheet layer materials in order to improve movement of the fluid through the topsheet layers and into the article. Suitable topsheet layer materials include, but are not limited to those described in U.S. Pat. No. 4,397,644 to Matthews et al.; U.S. Pat. No. 4,629,643 to Curro et al.; U.S. Pat. No. 5,188,625 Van Iten et al.; U.S. Pat. No. 5,382,400 to Pike et al.; U.S. Pat. No. 5,533,991 to Kirby et al.; U.S. Pat. No. 6,410,823 to Daley et al. and United States Publication 2012/0289917 to Abuto et al., each of which is hereby incorporated by reference thereto in its entirety.

In one desirable embodiment the first and second topsheet layer materials may be constructed of any woven or nonwoven material which passes body fluids, yet remains comfortable to the user. Suitable nonwoven materials include, but are not limited to, hydroentangled spunlace materials, bonded carded webs (BCW) made from staple fibers, and spunbond webs. The basis weight of nonwoven webs may generally vary, such as from about 5 grams per square meter ('gsm') to 150 gsm, in some embodiments from about 10 gsm to about 125 gsm, and in some embodiments, from about 25 gsm to about 120 gsm. As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in its entirety by reference thereto for all purposes. Spunbond fibers are generally not tacky when they are deposited onto a collecting surface. Spunbond fibers may sometimes have diameters less than about 40 microns, and often between about 5 to about 20 microns. Further examples of suitable topsheet materials include rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid. Other suitable topsheet layer materials include through-air bonded carded webs (TABCW) made from staple length fibers such as a 25 gram per square meter (gem) web made with 1.5 denier (d), polyethylene sheath, polypropylene core bicomponent, 35-40 millimeter (mm) staple length fibers available from FiberVisions Corporation with offices in Duluth, Ga., USA which are available under the trade designation ESC215.

The first and second topsheet layer materials may also each be made from two or more different nonwoven or film materials, with the different materials placed in separate locations laterally across the topsheet layer. For example, the first topsheet layer 22 may be a two layer or multi-component material with a central section positioned along and straddling the longitudinal center direction of the product, with lateral side-cover sections flanking and joined to each side (or side edge) of the central section. The central section may be made for example, from the aforementioned TABCW materials or it may be made from an apertured film. The lateral side sections may be made from a different fibrous nonwoven material which is joined to the central longitudinally directed section. Such a two layer (also known as dual cover) configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. Such a two layer topsheet material (or bicomponent topsheet) can offer the feeling of dryness in the center longitudinally direction section, and a soft feeling along the side longitudinally directed sections. It is also contemplated that such two layer topsheet materials may additionally include elastic or shrinkable components to lift up portions of the materials during use. While not illustrated, the first and second topsheet layers may be apertured to allow for more rapid penetration of body fluid into the absorbent article.

As noted, the backsheet layer 17 or outercover, functions to isolate absorbed fluids from the wearer's garments or bedding, and therefore desirably comprises a liquid-impervious material. In one aspect, the backsheet layer 17 may optionally comprise a material that prevents the passage of liquids but allows air and water-vapor to pass there-through. The backsheet layer can comprise a single layer or multiple layers, and these one or more layers can themselves comprise similar or different materials. Suitable backsheet layer materials include, but are not limited to, polyolefin films, nonwovens and nonwoven laminates, and film/nonwoven laminates. The particular structure and composition of the backsheet layer 17 may be selected from various known films and/or fabrics with the particular material being selected as appropriate to provide the desired level of liquid barrier, strength, abrasion resistance, tactile properties, aesthetics and so forth. Suitable backsheet layer materials include, but are not limited to, those described in U.S. Pat. No. 4,578,069 to Whitehead et al.; U.S. Pat. No. 4,376,799 to Tusim et al.; U.S. Pat. No. 5,695,849 to Shawver et al; U.S. Pat. No. 6,075,179 et al. to McCormack et al. and U.S. Pat. No. 6,376,095 to Cheung et al., each of which are hereby incorporated by reference thereto in its entirety.

Between the liquid pervious first topsheet layer 22 and the liquid impervious backsheet layer (outercover) 17 may be positioned at least a first absorbent core layer 32. For example, as illustrated, the pad includes one absorbent core layer 32. The absorbent core layer functions to absorb and preferably "lock-up" and retain the bodily fluids that pass into the absorbent article through the first and second topsheet layers. The first absorbent core layer 32 can comprise a single layer or multiple layers and these one or more layers can themselves comprise similar or different materials. In order to efficiently and effectively utilize the absorbent capacity of the article, it is common for the absorbent structure to include one or more surge layers, liquid distribution layers or wicking layers in combination with a highly absorbent core layer that preferentially absorbs and retains the liquids. Suitable wicking layers include, but are not limited to, bonded-carded webs, hydroentangled nonwoven webs, or spunbond webs containing fibers treated with or containing one or more topical agents that improve the contact angle with the bodily fluid and/or modify the flow properties of the bodily fluid. Highly absorbent core layers often include, but are not limited to, batts or webs containing wood pulp fibers, superabsorbent particles (also known as SAP or SAM), synthetic wood pulp fibers, synthetic fibers and combinations thereof. The absorbent core layer 32 may comprise any one of a number of materials and structures, the particular selection of which will vary with the desired loading capacity, flexibility, body fluid to be absorbed and other factors known to those skilled in the art. By way of example, suitable materials and/or structures for the absorbent core layer include, but are not limited to, those described in U.S. Pat. No. 4,610,678 to Weisman et al.; U.S. Pat. No. 6,060,636 to Yahiaoui et al.; U.S. Pat. No. 6,610,903 to Latimer et al.; U.S. Pat. No. 7,358,282 to Krueger et al. and United States patent publication 20100174260 to Di Luccio et al., each of which is hereby incorporated by reference thereto in its entirety.

The shape of the first absorbent core layer 32 can vary as desired and can comprise any one of various shapes including, but not limited to, generally triangular, rectangular, dog-bone and elliptical shapes. In one embodiment, the absorbent core layer 32 has a shape that generally corresponds with the overall shape of the sanitary pad 10, 200 such that the first absorbent core layer 32 terminates proximate the peripheral seal region 25 and wings 16. The dimensions of the first absorbent core layer 32 can be substantially similar to those of the sanitary pad 10, 200; however it will be appreciated that the dimensions of the absorbent core layer 32 while similar, will often be slightly less than those of the overall sanitary pad 10, 200 in order to be adequately contained therein, and desirably sealed around it's edges. As previously indicated, the absorbent core layer 32 is positioned between the first topsheet layer 22 and backsheet 17 layer, which make up the lower pad structure 152.

As noted also, the pad 10, 200 includes a folded upper pad structure 150, including a second topsheet layer 26. The second topsheet layer folds about either a transfer layer 33, a second absorbent core layer 30, another lofty layer, or a combination thereof. Such transfer layer may be constructed from a lofty layer such as for example an airlaid material as is known in the art. In one embodiment, such airlaid material is between 1 and 2 mm in thickness and demonstrates a basis weight of between 50 and 100 gsm and a density desirably of about 50 kg/m3. In an alternative embodiment, the upper pad structure includes an absorbent core layer which is comprised of at least of fluff material. In one embodiment, the fluff layer has a thickness of between about 4 and 6 mm, a basis weight of between about 175 and 300 gsm, and a density of between about 43 and 75 kg/m3.

The individual layers comprising the pad/article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. In one embodiment, the first absorbent core layer 32 can be sealed between the first topsheet layer 22 and backsheet layer 17 along the perimeter of the absorbent first absorbent core layer 32 along sealing region 25 formed by the application of heat and pressure to melt thermoplastic polymers located in the first topsheet layer 22 and/or backsheet layer 17.

The wings 16 can be constructed from materials described above with respect to the topsheet layers and backsheet layer. In one embodiment, the wings can comprise an extension of a layer of material within the topsheet layer(s) and/or backsheet layer. By way of example, the wings 16, can be formed by an extension of the topsheet layer(s) and backsheet layer 17 that are welded together along sealing region 25. Such wings can be integrally formed with the main portion of the absorbent article. Alternatively, the wings can be formed independently and separately attached to an intermediate section of the article. Wings that are made independent of the other components of the absorbent article can be welded onto or adhesively joined to a portion of the topsheet layer(s) and/or backsheet layer. In addition, as is known in the art, when cutting materials to the desired shape it is preferable to arrange the components so as to minimize waste. Examples of processes for manufacturing absorbent articles and wings include, but are not limited to those described in U.S. Pat. No. 4,059,114 to Richards; U.S. Pat. No. 4,862,574 to Hassim et al., U.S. Pat. No. 5,342,647 to Heindel et al., U.S. Pat. No. 7,070,672 to Alcantara et al., international publication WO1997040804 to Emenaker et al., and United States patent publication 20040040650 to Venturino et al., each of which are hereby incorporated by reference thereto in its entirety.

As noted, in order to further assist with the maintenance of the feminine hygiene pad 10, 200 in the desired location on the undergarment, garment adhesive patches may be applied to the garment facing side of the backsheet layer 17. The use of garment adhesive on the backsheet to help secure placement of an absorbent article on the garment is well known in the art and there are numerous adhesive patterns and releasable peel strips suitable for use with the present invention. Examples of suitable garment adhesives, patterns and release sheets include, but are not limited to, those described in DE700225U1; U.S. Pat. No. 3,881,490 to Whitehead et al.; U.S. Pat. No. 3,913,580 Ginocchio; U.S. Pat. No. 4,337,772 to Roeder et al.; GB1349962; and United States patent publication 20070073255A1 to Thomas et al., each of which are hereby incorporated by reference thereto in its entirety. The absorbent articles/feminine hygiene pads of the present invention may further include one or more additional aesthetic or functional components or elements as may be desired. By way of example, the absorbent article may optionally include slits, voids or non-coordinated embossing on the topsheet layer, interior layers, and/or absorbent core layer, in order to improve fluid intake, fluid distribution, stiffness (bending resistance) and/or aesthetic appeal. Examples of additional suitable embossing patterns and methods of embossing such concave embossments/indentations include, but are not limited to, those are described in U.S. Pat. No. 4,781,710 Megison et al.; U.S.

Pat. No. 7,686,790 to Rasmussen et al., EP0769284A1 to Mizutani et al.; and United States publication 20050182374 to Zander et al., each of which are hereby incorporated by reference thereto in its entirety.

The contemplated personal care absorbent articles can optionally contain one or more additional elements or components as are known and used in the art including, but not limited to, the use of fold lines, individual wrappers, elasticated flaps that extend above the plane of the topsheet layer in use, additional independent wings such as about the ends, odor control agents, perfumes, and the use of ink printing on one or more surfaces of the topsheet layers, backsheet layer, wings, interiorly-situated layer(s) and/or absorbent core layers. Still further additional features and various constructions are known in the art.

The pads including the inventive side barrier features 80, can be manufactured by the placement of a folded layered upper structure 150 upon a lower layered structure 152, and then selectively bonding/embossing areas of the pad so as to create side barriers that are elevated without the use of expensive polymer strands or additional lateral layers. By including the side barrier features 80 in articles, a lofty, pillowy structure is created that offers targeted side barrier protection adjacent high leakage potential areas. Such side barrier features 80 also include non-parallel side edges (such as 11A and 85) which better conform to the inner thighs of a user.

While the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

The invention claimed is:

1. An absorbent article having non-uniform dimensioned side barrier features, the absorbent article including a longitudinal direction, a transverse direction and a depth direction, and having longitudinally directed side edges and longitudinal ends comprising:
  a lower structure having longitudinally directed side edges, said lower structure including a backsheet layer, a first fluid permeable topsheet layer bonded to said backsheet layer, and a first absorbent core layer sandwiched between said first fluid permeable topsheet layer and said backsheet layer, said first absorbent core layer having lateral-most side edges,
  an upper structure in fluid communication with said lower structure, said upper structure adjacent and bonded to said lower structure on said first fluid permeable topsheet layer, and including a second fluid permeable topsheet layer and at least one absorbent additional layer selected from the group consisting of a transfer layer, a second absorbent core layer, a lofty layer,
  wherein said second fluid permeable topsheet layer is folded about the at least one additional layer to create substantially straight side barrier feature lateral-most edges, said side barrier feature lateral-most edges being inboard of said lateral-most side edges of said first absorbent core layer, said upper structure bonded to said lower structure at said side barrier feature lateral-most edges, and at least at one of said article longitudinal ends,
  wherein said upper structure includes embossment channels or embossment features which extend in the longitudinal direction of said article and, when the article is viewed in a top plan view, the embossment channels or embossment features have a concave curve-shaped configuration in the transverse direction of the absorbent article with respect to said substantially straight side barrier feature lateral-most edges, and said embossment channels or embossment features are within at least two layers of said upper structure of said article, such that said concave curve-shaped embossment channels or embossment features and said substantially straight side barrier feature lateral-most edges define side barrier features of the absorbent article, wherein said side barrier features have non-uniform lateral width dimensions when the lateral width dimensions of the side barrier features are measured between said concave curve-shaped embossment channels or embossment features and said substantially straight side barrier feature lateral-most edges along the longitudinal direction of said article, or a combination of non-uniform lateral width and non-uniform height dimensions along the longitudinal direction of said article, wherein said side barrier features are separable from and elevate above said lower structure along a portion of said side barrier feature lateral-most edges corresponding to said non-uniform width dimension, allowing said side barrier features to conform to the inner thighs of a user of said article, as a result of said non-uniform lateral width dimensions,
  the absorbent article further comprising wings extending laterally along the article longitudinally directed side edges wherein said concave curve-shaped embossment channels or embossment features are concave in the transverse direction of the absorbent article with respect to said side barrier lateral-most edges adjacent to said wings.

2. The absorbent article of claim 1, wherein said upper structure includes a second fluid permeable topsheet layer, and a transfer layer subjacent said second fluid permeable topsheet layer.

3. The absorbent article of claim 2, wherein said upper structure further includes a second absorbent core layer subjacent said transfer layer.

4. The absorbent article of claim 1, wherein said upper structure includes a second fluid permeable topsheet layer and a second absorbent core layer subjacent said second fluid permeable topsheet layer.

5. The absorbent article of claim 1, wherein said embossment channels comprise continuous concave channels separated by a minimum distance of between about 20 and 40 mm.

6. The absorbent article of claim 1, wherein said side barrier features have a lateral width range of between an amount greater than 0, to about 12 mm, and wherein the widest lateral width is positioned adjacent to said wings.

7. The absorbent article of claim 6, wherein said side barrier features have a lateral width of between about 6 and 10 mm in at least one location along said article longitudinal direction.

8. The absorbent article of claim 6, wherein said side barrier features have a height range of between about 1 and 12 mm along the article longitudinal direction, and wherein the largest side barrier height is positioned adjacent to said wings.

9. The absorbent article of claim 6, wherein said side barrier features are positioned closer to one longitudinal end than the other longitudinal end.

10. The absorbent article of claim 6, wherein said embossment channels or embossment features extend downwardly through at least three layers within said article.

11. The absorbent article of claim 10, wherein said embossment channels or embossment features extend downwardly through at least four layers within said article.

12. The absorbent article of claim 1, wherein said first fluid permeable topsheet layer is noncontinuous along the transverse direction.

13. The absorbent article of claim 1, wherein said upper structure has a basis weight of all layers excluding said second fluid permeable topsheet layer of between about 18 and 350 gsm.

14. The absorbent article of claim 1, wherein said second fluid permeable topsheet layer does not completely envelop said absorbent additional layer or layers.

15. The absorbent article of claim 14, wherein said side barrier features of said upper structure are not bonded to said lower structure along said side barrier features' lateral-most edges, for a length of between about 110 and 130 mm of said side barrier features.

16. The absorbent article of claim 1, wherein said upper structure includes a second absorbent core layer, and said second absorbent core layer has a second absorbent core layer transverse direction width, said first absorbent core layer has a first absorbent core layer transverse width, and said ratio of said second absorbent core layer transverse width to said first absorbent core layer transverse width is between about 0.7 to about 0.9.

17. The absorbent article of claim 1, wherein said side barrier features of said upper structure are not bonded to said lower structure along said side barrier features' lateral-most edges, for a length of between about 70 and 200 mm of said side barrier features.

18. The absorbent article of claim 1, wherein said side barrier features demonstrate a non-uniform lateral width and non-uniform height dimension along the article longitudinal direction.

19. The absorbent article of claim 1, wherein said article includes a central longitudinal direction and said side barrier features are symmetrically positioned about the article central longitudinal direction.

20. The absorbent article of claim 1, wherein said article includes side barrier features closer to one longitudinal end than the other longitudinal end.

21. The absorbent article of claim 1, wherein said side barrier features are visually highlighted by printing.

22. The absorbent article of claim 1, wherein said upper structure is bonded to said lower structure at said side barrier feature lateral-most edges, at both of said article longitudinal ends.

23. The absorbent article of claim 1, wherein said upper structure is bonded to said lower structure at said side barrier feature lateral-most edges, at one of said article longitudinal ends and also at a position substantially inboard of the other article longitudinal end, at a position towards the center of the pad.

* * * * *